(12) United States Patent
Cabrera et al.

(10) Patent No.: US 10,729,443 B2
(45) Date of Patent: Aug. 4, 2020

(54) ADAPTER, EXTENSION, AND CONNECTOR ASSEMBLIES FOR SURGICAL DEVICES

(71) Applicant: Covidien LP, Mansfield, MA (US)

(72) Inventors: Ramiro Cabrera, Cheshire, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 465 days.

(21) Appl. No.: 15/238,049

(22) Filed: Aug. 16, 2016

(65) Prior Publication Data

US 2016/0354088 A1    Dec. 8, 2016

Related U.S. Application Data

(63) Continuation-in-part of application No. 14/875,766, filed on Oct. 6, 2015, now Pat. No. 10,226,254.
(Continued)

(51) Int. Cl.
*A61B 17/29* (2006.01)
*A61B 17/115* (2006.01)
(Continued)

(52) U.S. Cl.
CPC .... *A61B 17/1155* (2013.01); *A61B 17/00234* (2013.01); *F16H 25/2056* (2013.01);
(Continued)

(58) Field of Classification Search
CPC . A61B 17/068; A61B 17/115; A61B 17/1155; A61B 2017/0046;
(Continued)

(56) References Cited

U.S. PATENT DOCUMENTS 2,777,340 A    1/1957   Hettwer et al.
2,957,353 A   10/1960   Babacz
(Continued)

FOREIGN PATENT DOCUMENTS

CA   2451558 A1   1/2003
CA   2824590 A1   4/2014
(Continued)

OTHER PUBLICATIONS

Partial European Search Report issued in corresponding European Application No. 15190643 dated Feb. 26, 2016.
(Continued)

*Primary Examiner* — Darwin P Erezo
*Assistant Examiner* — Christian D Knauss
(74) *Attorney, Agent, or Firm* — Carter, DeLuca & Farrell LLP

(57) ABSTRACT

A surgical assembly for operably connecting an end effector to an electrosurgical instrument includes an adapter assembly and an extension assembly. The adapter assembly includes a drive coupling assembly, a drive transfer assembly operably received through the drive coupling assembly and including a first rotatable shaft, and a first pusher assembly operably connected to the first rotatable shaft for converting rotational motion from the first rotatable shaft to longitudinal movement to perform a first function. The first pusher assembly includes a first pusher member having an outer housing formed of a first material, and a threaded insert formed of a second material and disposed within the outer housing. The extension assembly is operably connected to a distal end of the adapter assembly, and includes a flexible band assembly operably connectable to the first pusher member of the first pusher assembly.

20 Claims, 30 Drawing Sheets

Related U.S. Application Data

(60) Provisional application No. 62/066,518, filed on Oct. 21, 2014, provisional application No. 62/251,930, filed on Nov. 6, 2015.

(51) Int. Cl.
  *F16H 25/20* (2006.01)
  *A61B 17/00* (2006.01)
  *A61B 17/072* (2006.01)

(52) U.S. Cl.
  CPC ........... *A61B 2017/00464* (2013.01); *A61B 2017/00473* (2013.01); *A61B 2017/00477* (2013.01); *A61B 2017/07285* (2013.01); *A61B 2017/2902* (2013.01); *A61B 2017/2905* (2013.01); *A61B 2017/2923* (2013.01); *F16H 2025/2087* (2013.01)

(58) Field of Classification Search
  CPC .. A61B 2017/00473; A61B 2017/2902; A61B 2017/00353; A61B 2017/00367; A61B 2017/2903; A61B 17/29; F16H 25/08; F16H 25/14; F16H 25/20556; F16H 2025/2087
  See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,681,979 B2 | 1/2004 | Whitman |
| 6,695,199 B2 | 2/2004 | Whitman |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,835,199 B2 | 12/2004 | McGuckin, Jr. et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |

(56) References Cited

U.S. PATENT DOCUMENTS

| | | |
|---|---|---|
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Soirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,590,763 B2 | 11/2013 | Milliman |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |

(56) References Cited

U.S. PATENT DOCUMENTS

| | | |
|---|---|---|
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2005/0165328 A1 | 7/2005 | Heske et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0241692 A1 | 10/2006 | McGuckin et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0036206 A1 | 2/2008 | Li-guo |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206136 A1* | 8/2009 | Moore ............. A61B 17/07207 227/176.1 |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1* | 4/2012 | Zemlok ............ A61B 17/07207 606/1 |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1* | 4/2013 | Kostrzewski .... A61B 17/07207 227/176.1 |
| 2013/0181035 A1 | 7/2013 | Willman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005677 A1* | 1/2014 | Shelton, IV ........... B23K 26/38 606/130 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0108201 A1 | 4/2015 | Williams |

(56) References Cited

U.S. PATENT DOCUMENTS

| | | |
|---|---|---|
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0190133 A1 | 7/2015 | Penna et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| CN | 102551840 A | 7/2012 |
| DE | 102008053842 A1 | 5/2010 |
| EP | 0705571 A1 | 4/1996 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2668910 A2 | 12/2013 |
| EP | 2684530 A1 | 1/2014 |
| EP | 2883504 A2 | 6/2015 |
| ES | 2333509 A1 | 2/2010 |
| JP | 08-038488 | 2/1996 |
| JP | 2005-125075 A | 5/2005 |
| KR | 20120022521 A | 3/2012 |
| WO | 2006026520 A2 | 3/2006 |
| WO | 2008045333 A2 | 4/2008 |
| WO | 2011/108840 A2 | 9/2011 |
| WO | 2012/040984 A1 | 4/2012 |
| WO | 2012/0166499 A1 | 12/2012 |
| WO | 2015041845 A2 | 3/2015 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action dated Dec. 12, 2018, issued in Chinese Appln. No. 201510843610.
Japanese Office Action dated May 28, 2019 (received Jun. 20, 2019), issued in JP Appln. No. 2015-206306.
European Search Report dated Dec. 6, 2019, issued in EP Appln. No. 19192171.
European Search Report dated Dec. 13, 2019, issued in EP Appln. No. 19191409.
Chinese Office Action dated Sep. 4, 2019, issued in CN Appln. No. 201510843610.
Australian Office Action dated Jul. 23, 2019, issued in AU Appln. No. 2015243004.

* cited by examiner

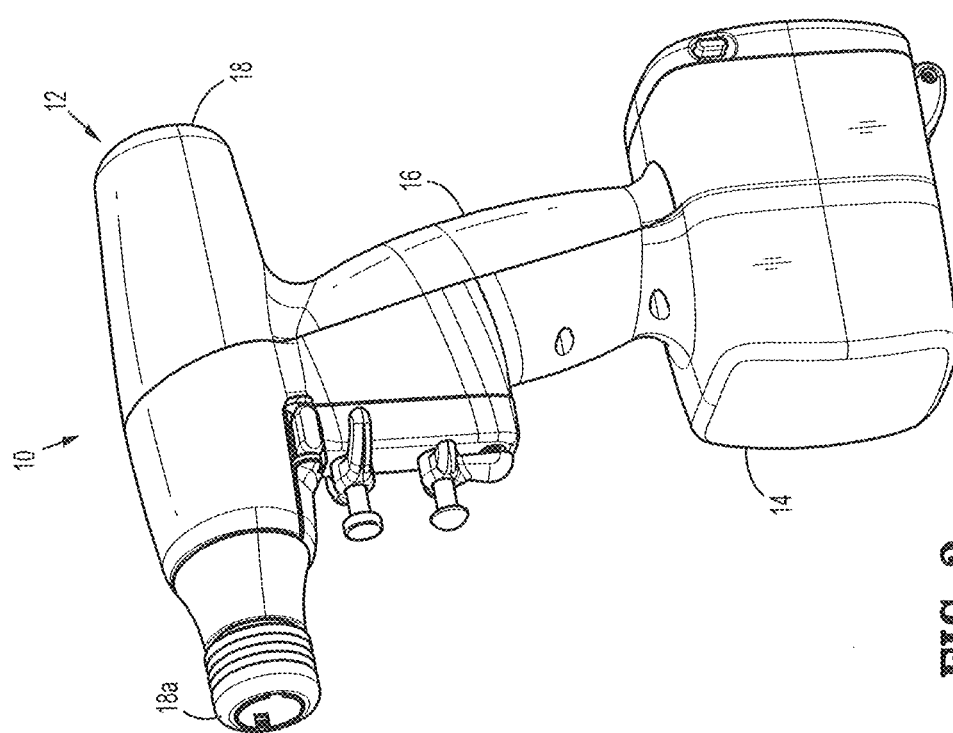

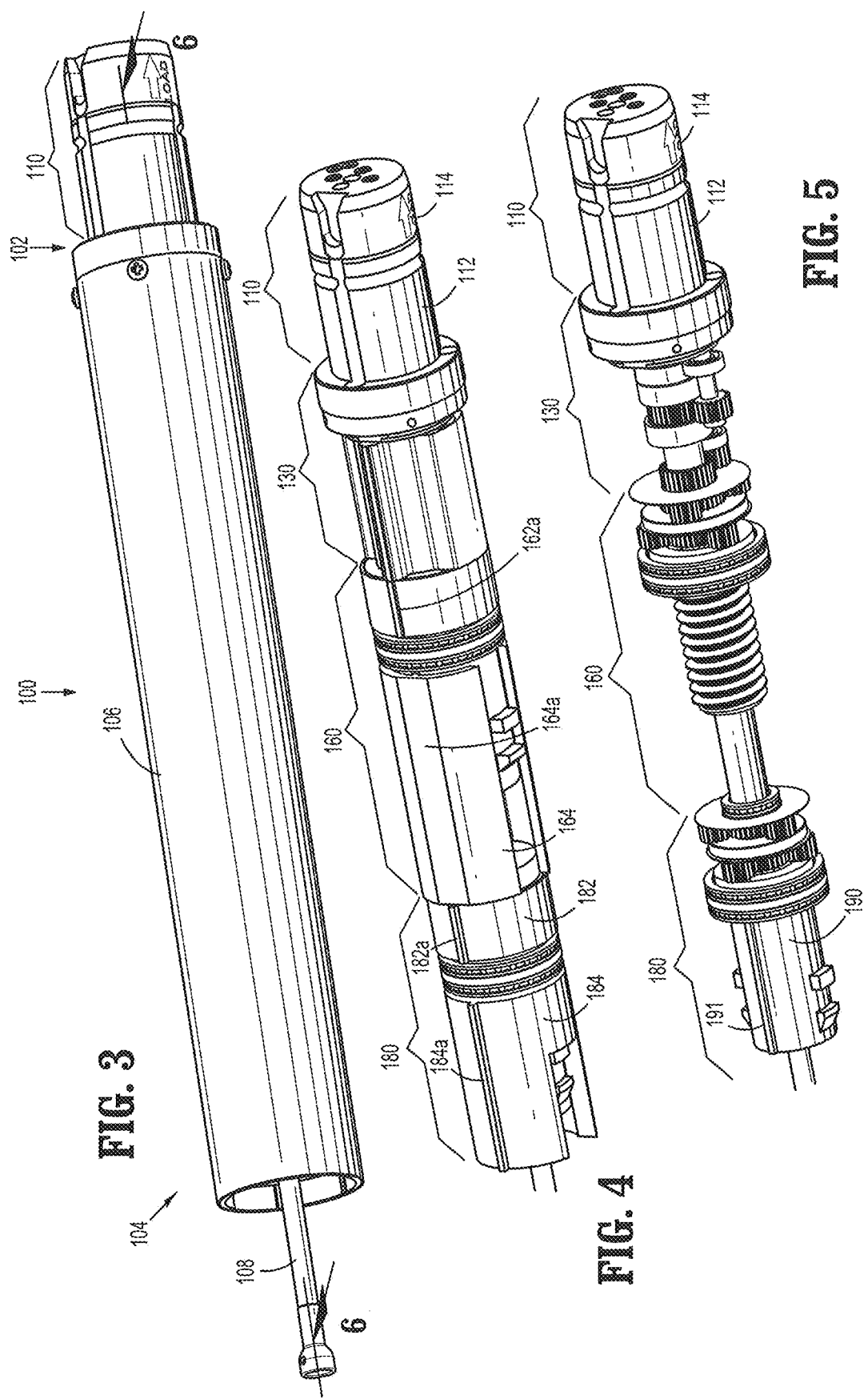

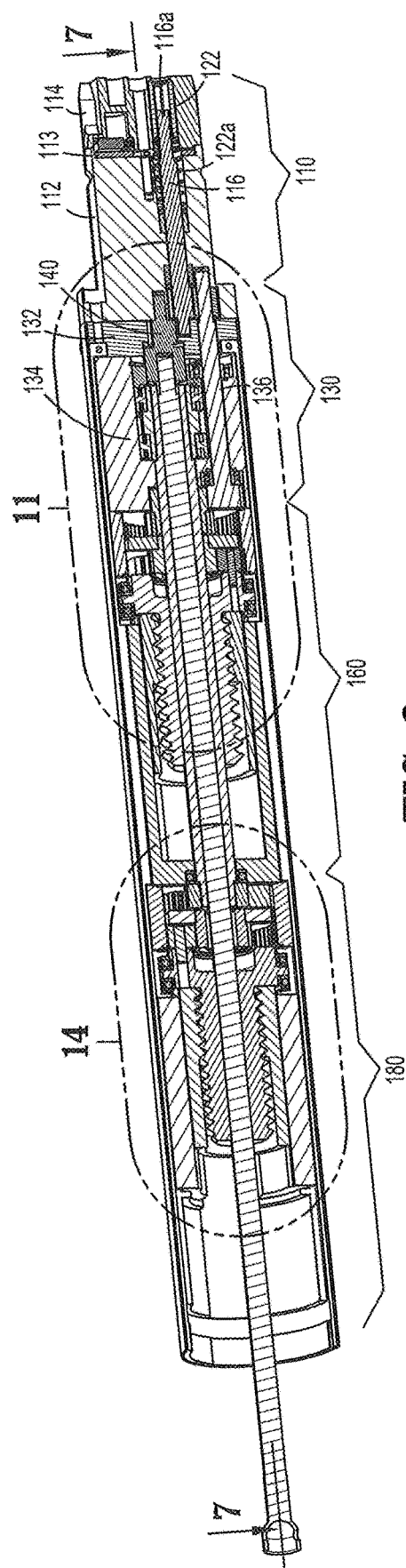
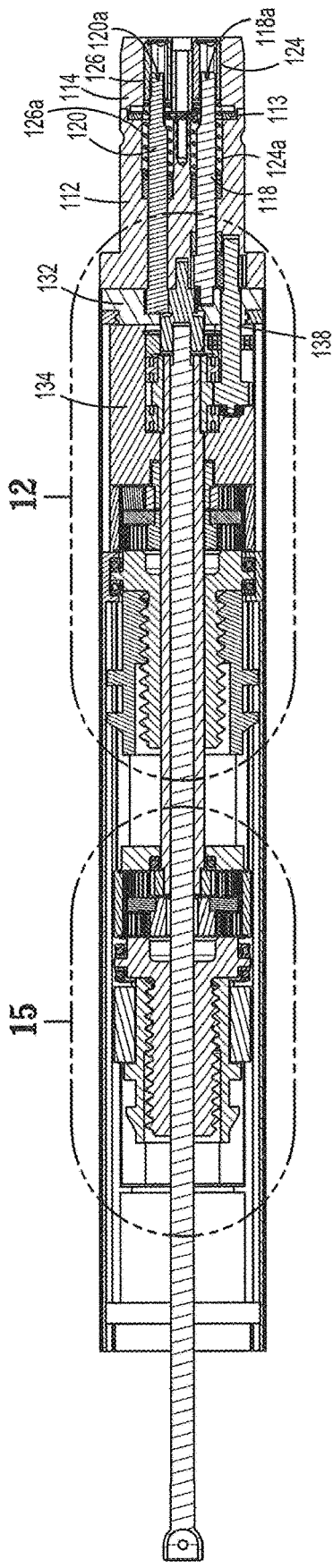
FIG. 6
FIG. 7

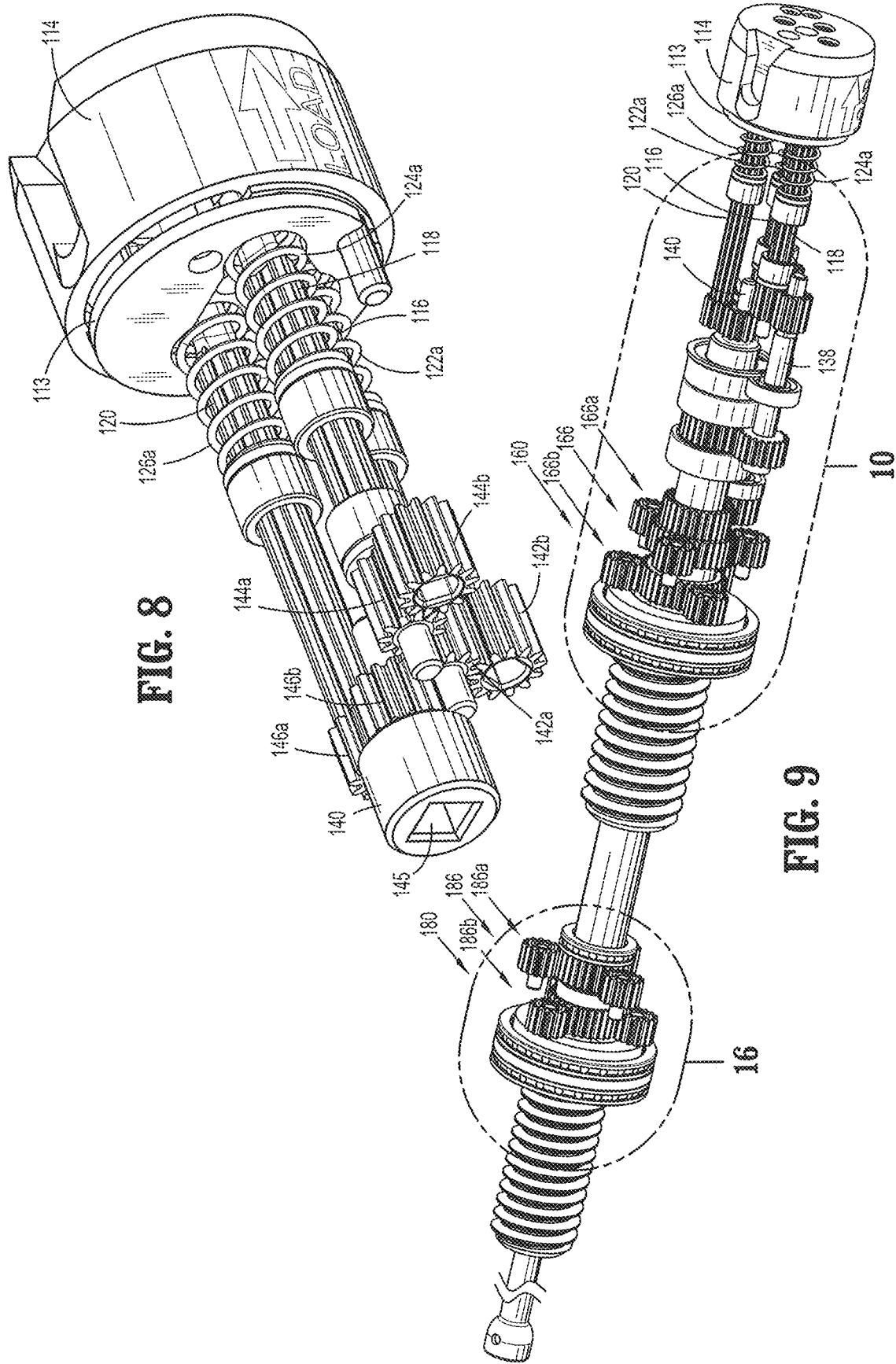

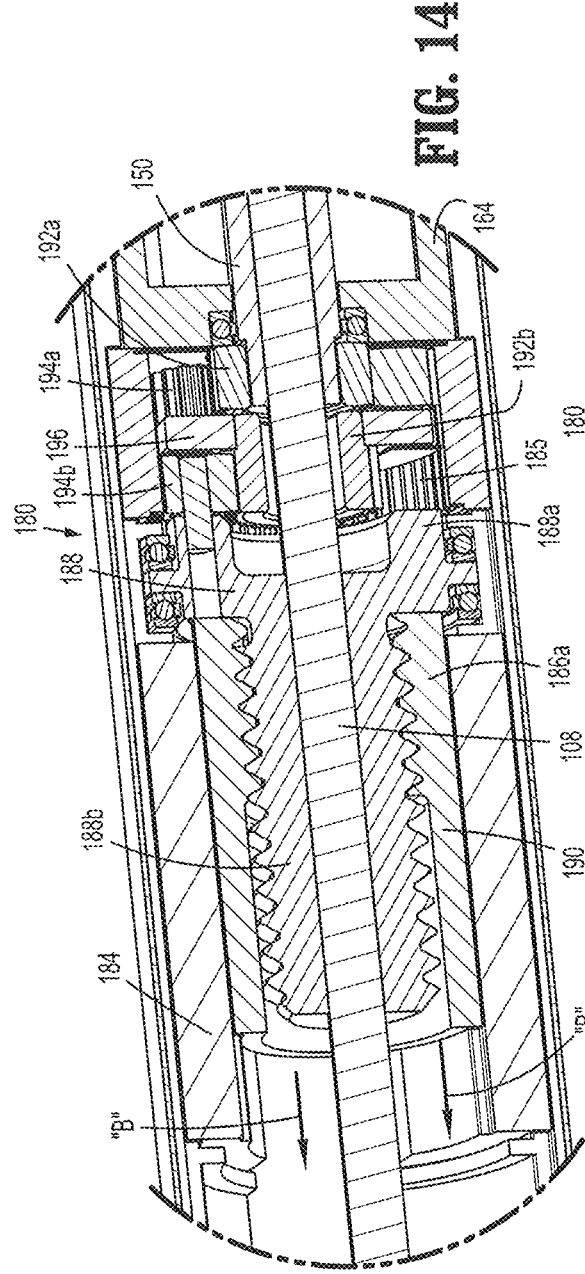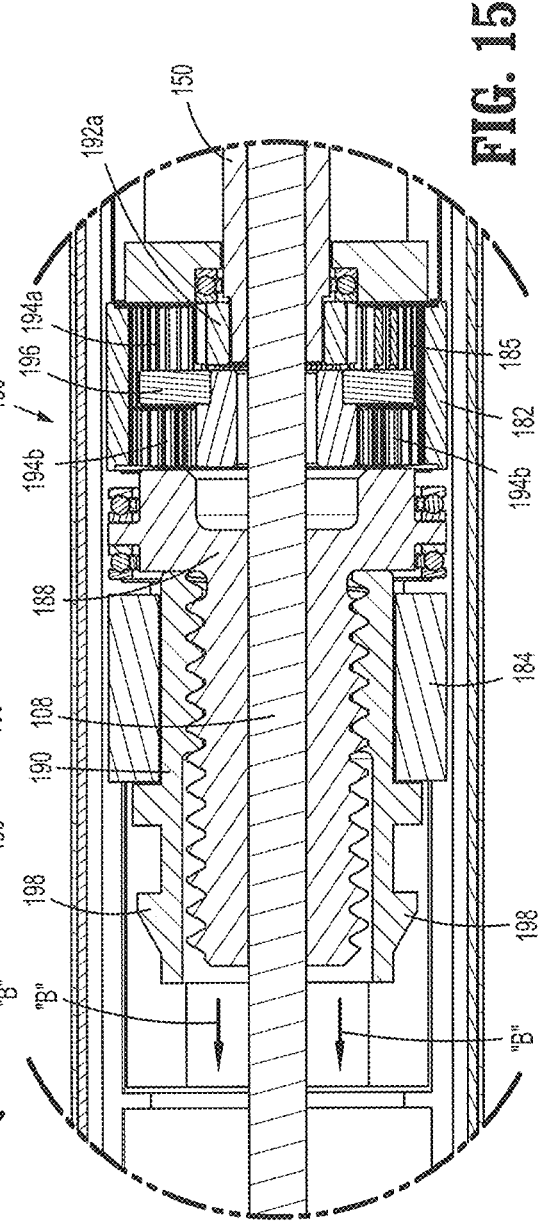

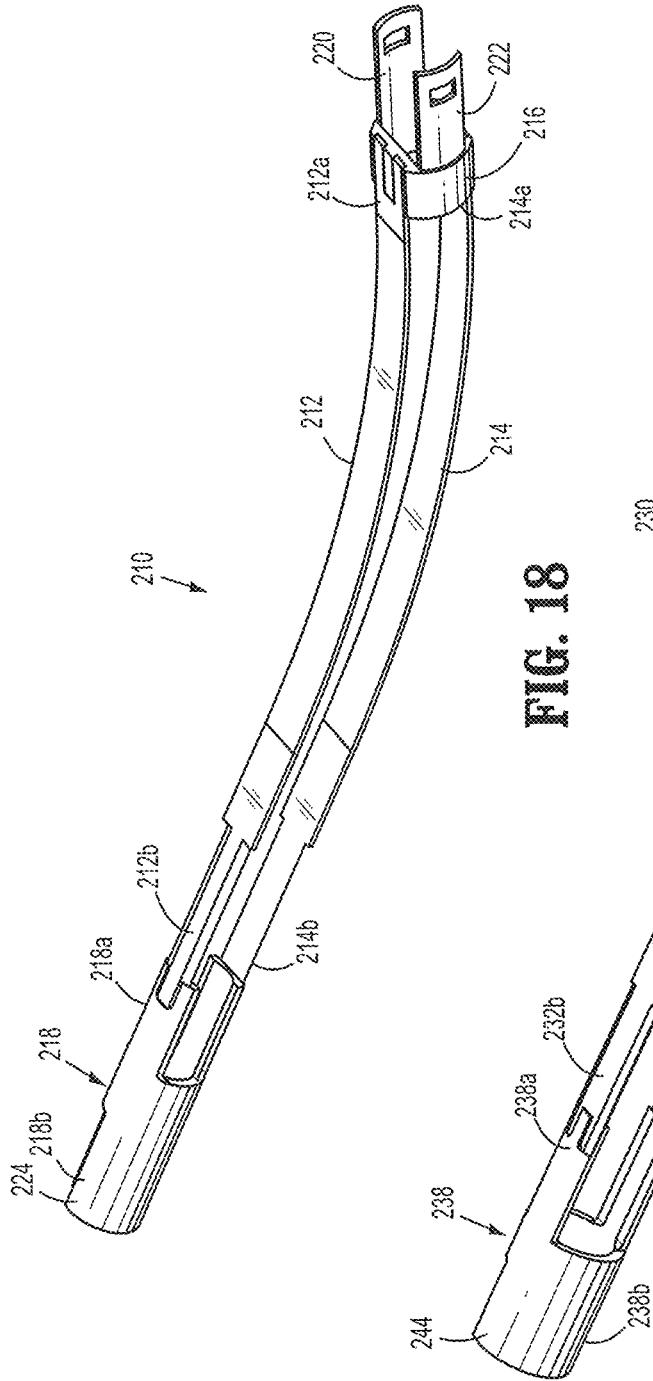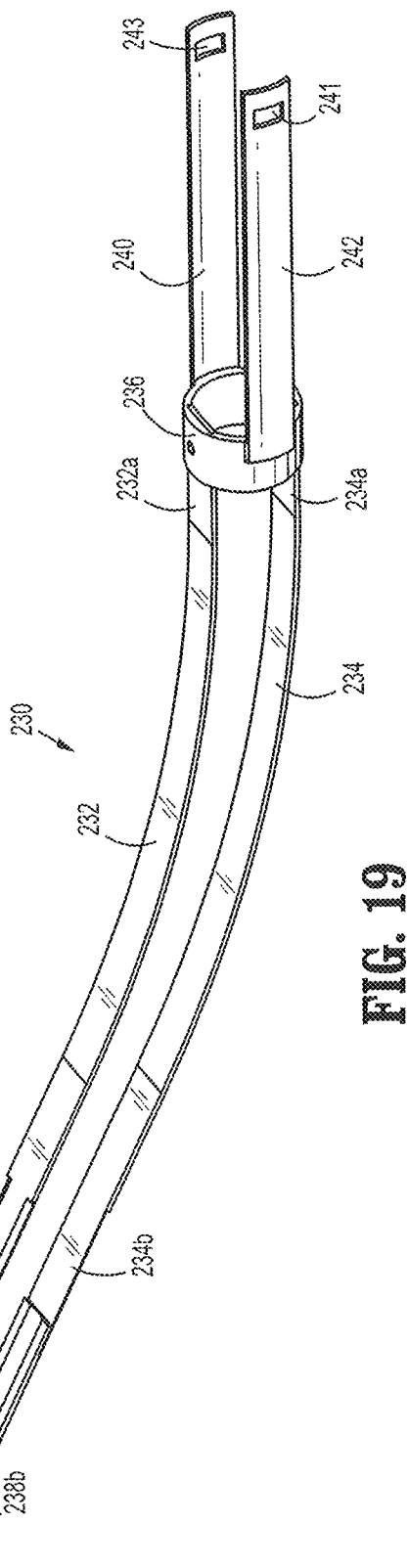

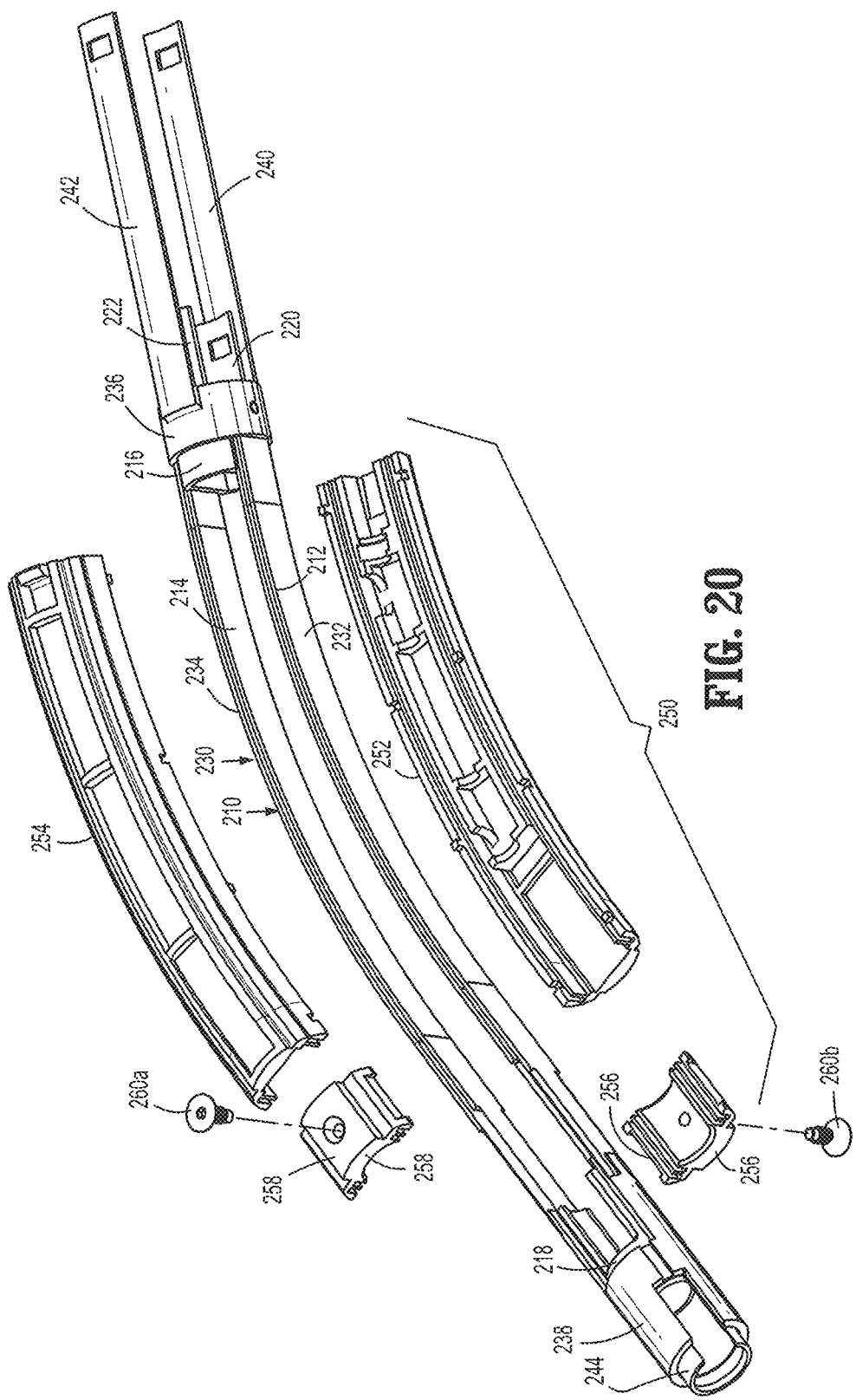

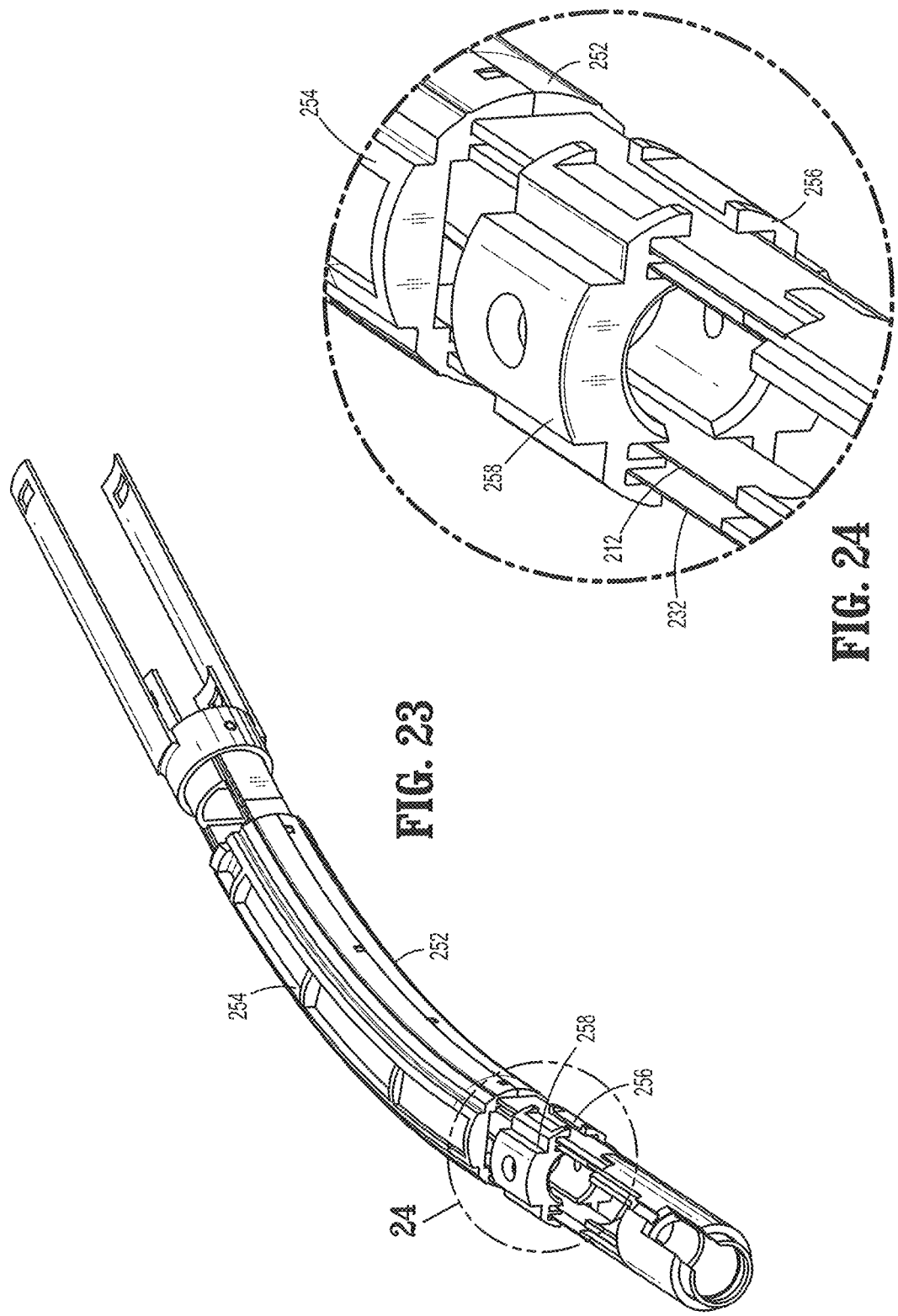

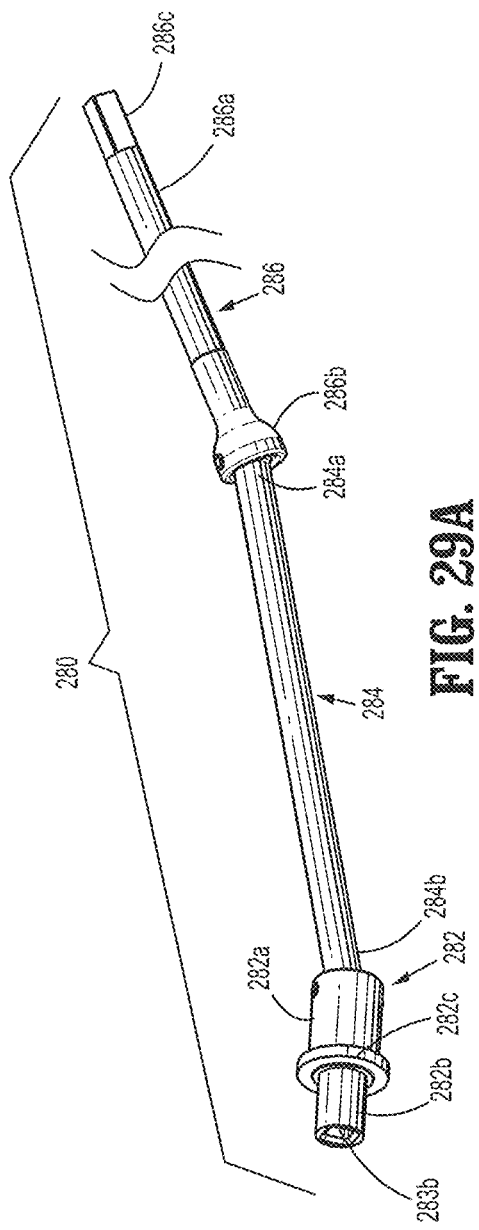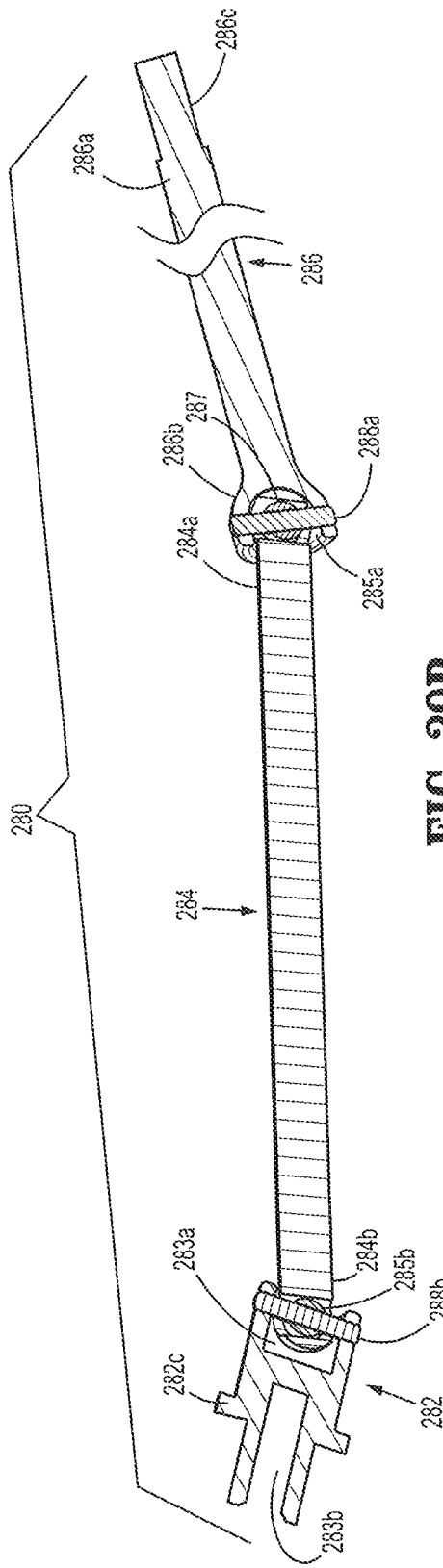

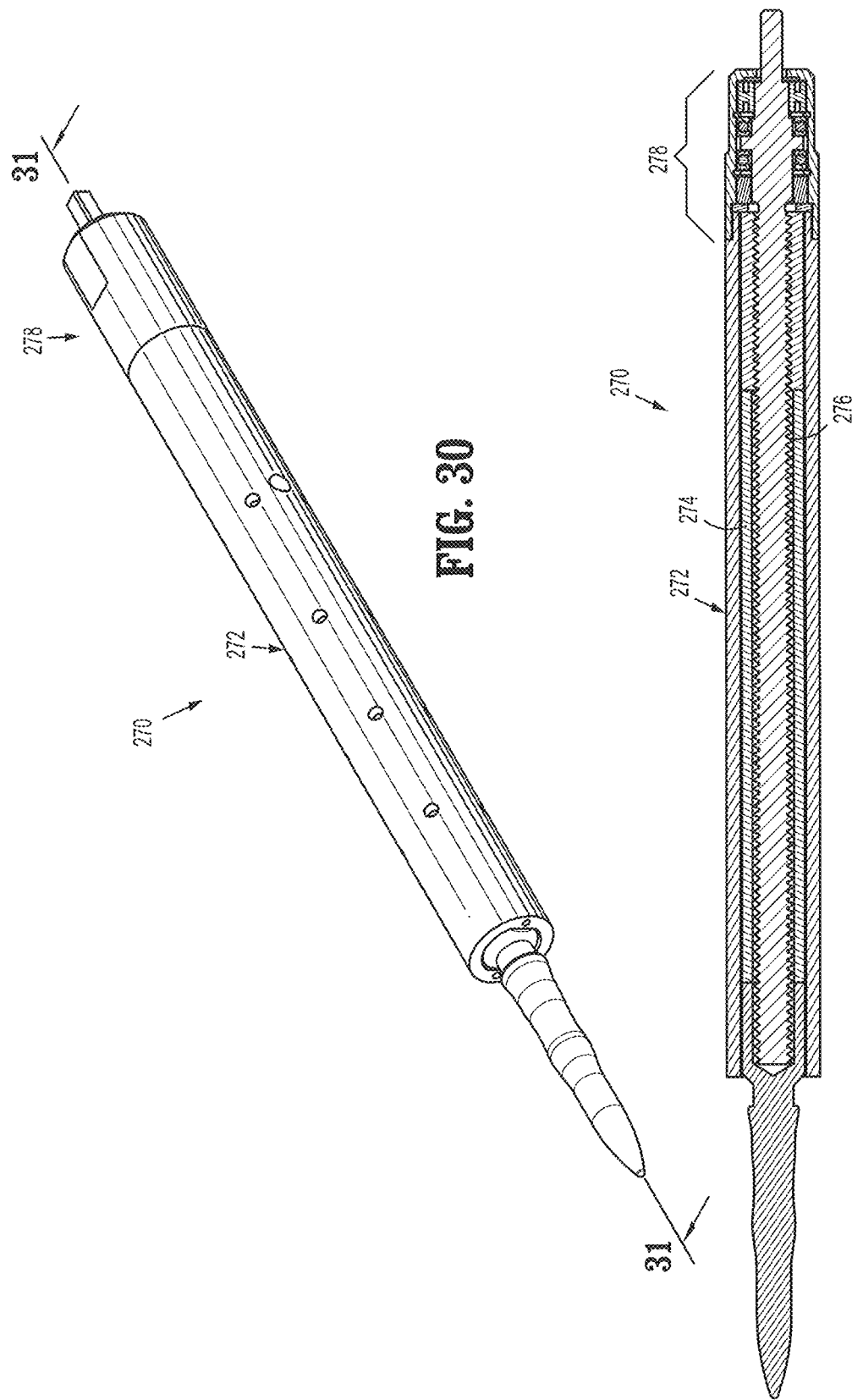

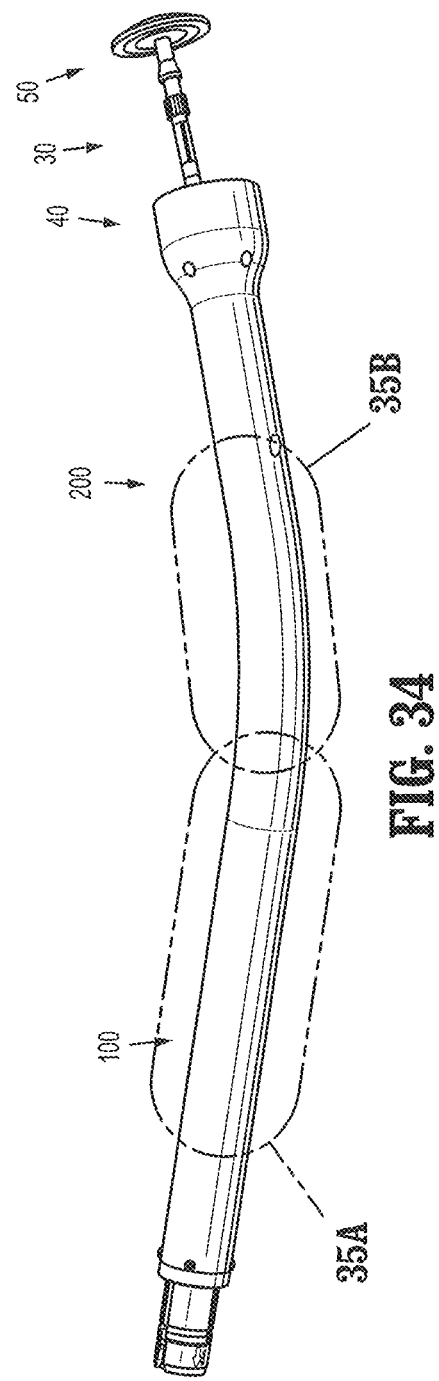

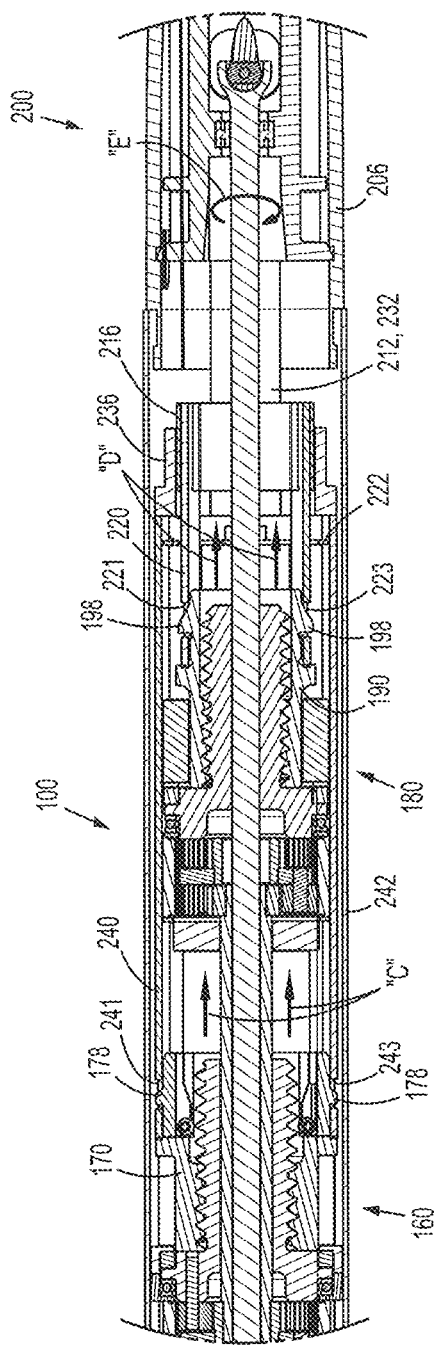
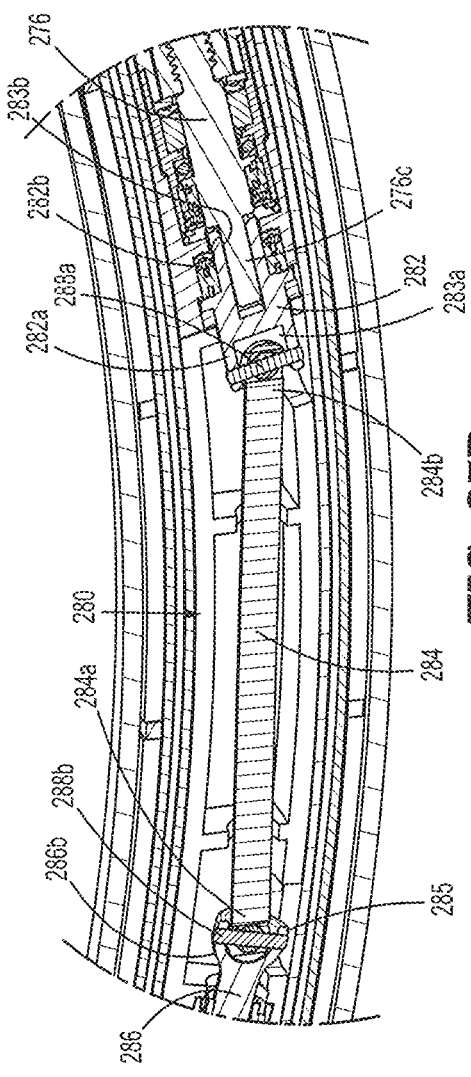
FIG. 35A
FIG. 35B

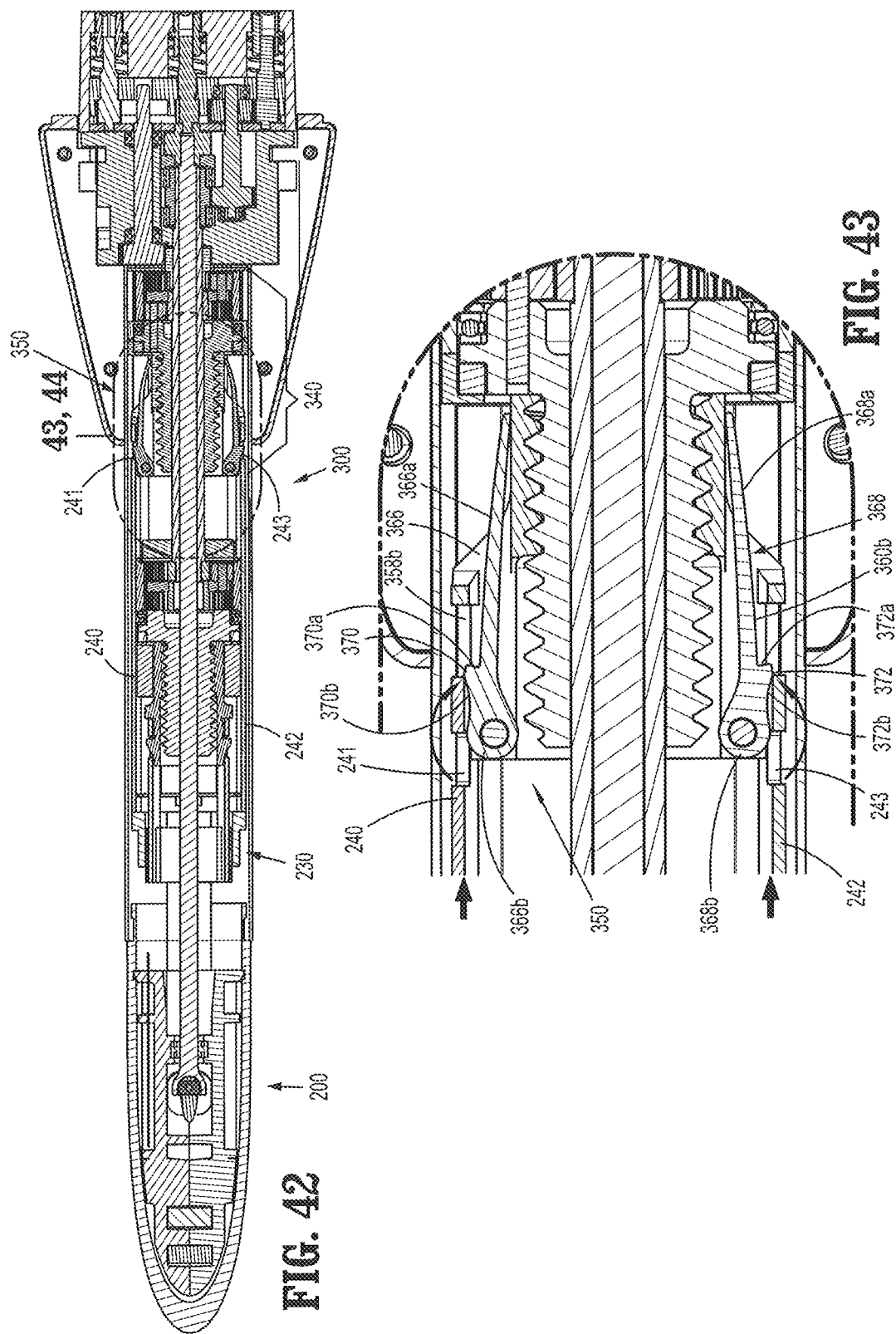

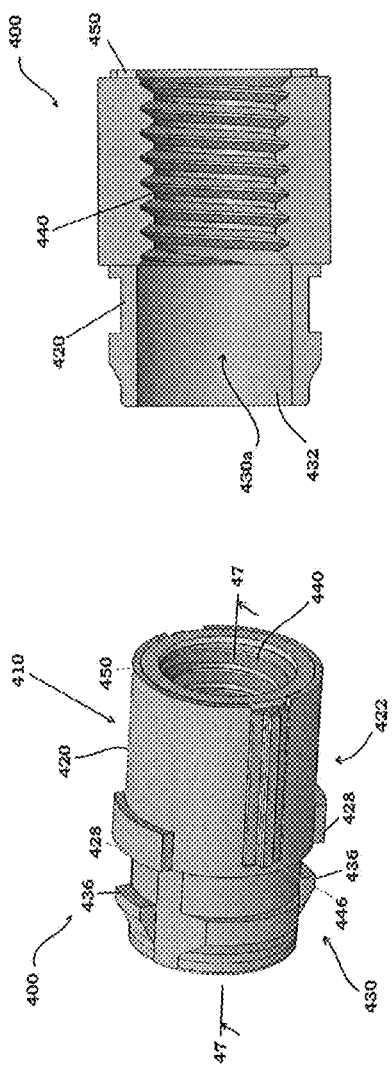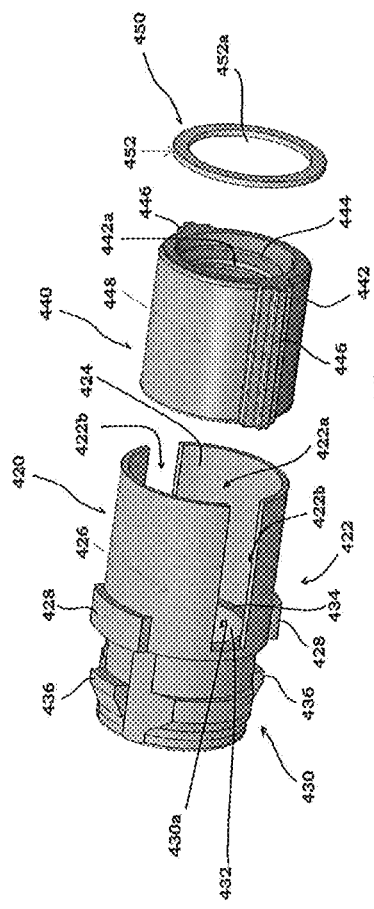

ADAPTER, EXTENSION, AND CONNECTOR ASSEMBLIES FOR SURGICAL DEVICES

CROSS-REFERENCE TO RELATED APPLICATIONS

The present application is a Continuation-in-Part Application claiming the benefit of and priority to U.S. patent application Ser. No. 14/875,766, filed on Oct. 6, 2015, which claims the benefit of and priority to U.S. Provisional Patent Application Ser. No. 62/066,518, filed on Oct. 21, 2014, the entire contents of each of which are incorporated by reference herein.

The present application also claims the benefit of and priority to U.S. Provisional Patent Application Ser. No. 62/251,930, filed on Nov. 6, 2015, the entire contents of each of which are incorporated by reference herein.

TECHNICAL FIELD

The present disclosure relates generally to powered surgical devices. More specifically, the present disclosure relates to an adapter assembly for selectively connecting an extension assembly including an end effector to the actuation units of the powered surgical devices.

BACKGROUND

Powered devices for use in surgical procedures are known. To permit reuse of the handle assemblies of these powered surgical devices and so that the handle assembly may be used with a variety of end effectors, adapter assemblies and extension assemblies have been developed for selective attachment to the handle assemblies and to a variety of end effectors. Following use, the adapter and/or extension assemblies may be disposed of along with the end effector. In some instances, the adapter assemblies and extension assemblies may be sterilized for reuse.

Many of the existing end effectors for use with many of the existing surgical devices and/or handle assemblies are driven by a linear force. For examples, linear force is typically required to operate end effectors for performing endo-gastrointestinal anastomosis procedures, end-to-end anastomosis procedures, and transverse anastomosis procedures. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, adapters and/or adapter assemblies are used to interface between and interconnect the linear driven extension assemblies and/or end effectors with the rotary driven surgical devices and/or handle assemblies.

SUMMARY

In accordance with an aspect of the present disclosure, a surgical assembly for operably connecting an end effector to an electrosurgical instrument includes an adapter assembly and an extension assembly. The adapter assembly includes a drive coupling assembly, a drive transfer assembly operably received through the drive coupling assembly and including a first rotatable shaft, and a first pusher assembly operably connected to the first rotatable shaft for converting rotational motion from the first rotatable shaft to longitudinal movement to perform a first function. The first pusher assembly includes a first pusher member having an outer housing formed of a first material, and a threaded insert formed of a second material and disposed within the outer housing. The extension assembly is operably connected to a distal end of the adapter assembly, and includes a flexible band assembly operably connectable to the first pusher member of the first pusher assembly.

The first material of the outer housing of the first pusher member may be a metal and/or the second material of the threaded insert of the first pusher member may be a polymer. In some embodiments, the metal is stainless steel and the polymer is polyether ether ketone.

The outer housing of the first pusher member may include first and second distal tabs extending laterally therefrom. The flexible band assembly may include first and second connector members, and each of the first and second connector members may be configured to engage a respective one of the first and second distal tabs. The outer housing of the first pusher member may include first and second proximal tabs extending laterally therefrom, and each of the first and second proximal tabs may be aligned with a respective one of the first and second distal tabs.

The threaded insert of the first pusher member may include an inner surface defining a threaded central bore. In some embodiments, the adapter assembly includes a screw member threadingly engaged with the inner surface of the threaded insert of the first pusher member.

The outer housing may include first and second apertures disposed therethrough, and the threaded insert may include an outer surface having first and second longitudinal rails extending laterally therefrom. Each of the first and second longitudinal rails of the threaded insert may be keyed to a respective one of the first and second apertures of the outer housing.

In embodiments, the first pusher member includes a retaining ring fixedly secured to a proximal end of the outer housing to secure the threaded insert within the outer housing. The retaining ring may be formed of a third material. The third material of the retaining ring may be a metal, and in some embodiments, the metal is stainless steel.

The surgical assembly may further include a second pusher assembly operably connected to a second rotatable shaft of the drive transfer assembly for converting rotational motion from the second rotatable shaft to longitudinal movement to perform a second function and/or a drive member operably connected to a third rotatable shaft of the drive transfer assembly for transferring rotational motion from the third rotatable shaft to perform a third function.

BRIEF DESCRIPTION OF THE DRAWINGS

Embodiments of the present disclosure are described herein with reference to the accompanying drawings, wherein:

FIG. 2 is a perspective side view of the exemplary electromechanical surgical device of FIG. 1;

FIG. 3 is a perspective side view of the adapter assembly of FIG. 1;

FIG. 4 is a perspective side view of the adapter assembly of FIG. 3 with the outer sleeve removed;

FIG. 5 is a perspective side view of the adapter assembly of FIGS. 3 and 4 with proximal and distal housings of first and second pusher assemblies removed;

FIG. 6 is a cross-sectional side view of the adapter assembly of FIGS. 2-4 taken along line 6-6 in FIG. 3;

FIG. 7 is a cross-sectional side view of the adapter assembly of FIGS. 2-5 taken along line 7-7 in FIG. 5;

FIG. 8 is an enlarged, perspective view of a coupling assembly and a transfer assembly of the adapter assembly of FIGS. 2-7;

FIG. 9 is a perspective side view of adapter assembly of FIGS. 2-7 with the housing assemblies removed;

FIG. 14 is an enlarged view of the indicated area of detail of FIG. 6;

FIG. 15 is an enlarged view of the indicated area of detail of FIG. 7;

FIG. 18 is a perspective side view of an inner flexible band assembly of the extension assembly of FIG. 17;

FIG. 19 is a perspective side view of an outer flexible band assembly of the extension assembly of FIG. 17;

FIG. 20 is a perspective side view of the inner and outer flexible band assemblies of FIGS. 18 and 19 and an exploded view of a frame assembly of the extension assembly of FIG. 17;

FIG. 23 is a front, perspective view of the inner and outer flexible band assemblies and frame assembly of FIG. 20;

FIG. 24 is an enlarged view of the indicated area of detail of FIG. 23;

FIG. 29A is a perspective side view of a link assembly of the extension assembly of FIG. 17;

FIG. 29B is a cross-section side view of the link assembly of FIG. 29A;

FIG. 30 is a perspective side view of the trocar assembly of FIG. 29;

FIG. 31 is a cross-sectional side view taken along line 31-31 of FIG. 30;

FIG. 34 is a perspective side view of the adapter assembly of FIG. 3 connected to the extension assembly of FIG. 17 and an end effector and an anvil assembly connected to the extension assembly;

FIG. 35A is an enlarged cross-sectional top view of the indicated area of detail of FIG. 34;

FIG. 35B is an enlarged cross-sectional side view of the indicated area of detail in FIG. 34;

FIG. 42 is a cross-sectional top view of the adapter assembly of FIG. 36 secured to the extension assembly of FIG. 17;

FIG. 43 is an enlarged cross-sectional top view of the indicated area of detail of FIG. 42, prior to full securement of the extension assembly to the adapter assembly;

FIG. 46 is a perspective side view of a pusher member in accordance with another embodiment of the present disclosure;

FIG. 47 is a cross-sectional side view taken along line 47-47 of FIG. 46; and

FIG. 48 is a perspective view, with parts separated, of the pusher member of FIGS. 46 and 47.

DETAILED DESCRIPTION OF EMBODIMENTS

Figure 1:
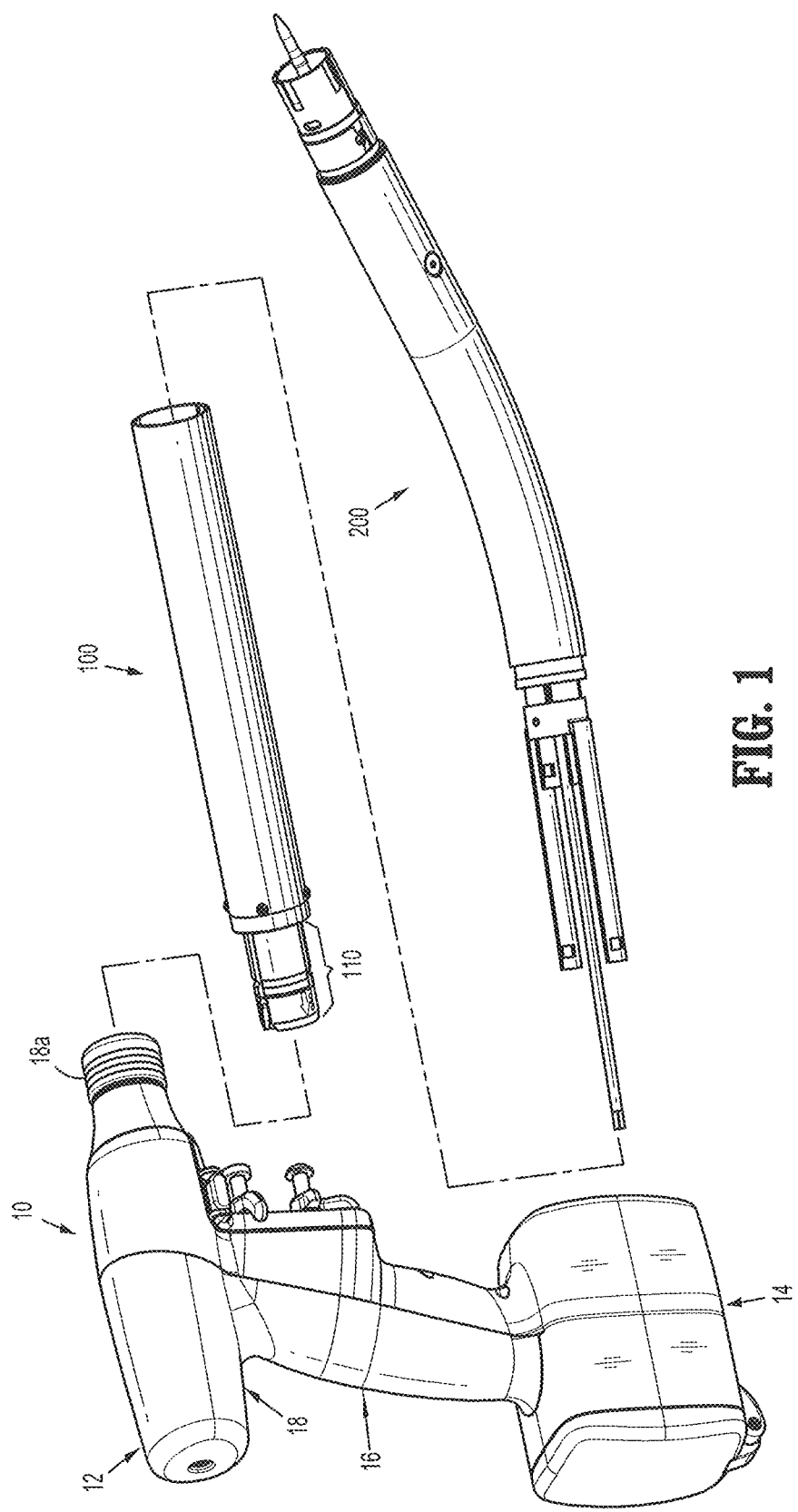
FIG. 1 is a perspective separated view of an adapter assembly, in accordance with an embodiment of the present disclosure, an extension assembly, in accordance with an embodiment of the present disclosure, and an exemplary electromechanical surgical device.

Embodiments of the presently disclosed adapter assemblies and extension assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as adapter assembly 100, is configured for selective connection to a powered handheld electromechanical instrument shown, generally as surgical device 10. As illustrated in FIG. 1, the surgical device 10 is configured for selective connection with the adapter assembly 100, and, in turn, the adapter assembly 100 is configured for selective connection with an extension assembly 200. The extension assembly 200 is configured for selective connection with a tool assembly or end effector, e.g. tool assembly 30 (FIG. 34), including a loading unit, e.g. loading unit 40 (FIG. 34), and an anvil assembly, e.g., anvil assembly 50 (FIG. 34), for applying a circular array of staples (not shown) to tissue (not shown).

As illustrated in FIGS. 1 and 2, the surgical device 10 includes a handle housing 12 having a lower housing portion 14, an intermediate housing portion 16 extending from and/or supported on the lower housing portion 14, and an upper housing portion 18 extending from and/or supported on the intermediate housing portion 16. A distal half-section of the upper housing portion 18 defines a nose or connecting portion 18a configured to accept a corresponding drive coupling assembly 110 (FIG. 10) of the adapter assembly 100. For a detailed description of the structure and function of an exemplary electromechanical instrument, please refer to commonly owned U.S. Pat. Appl. Publ. No. 2012/0253329 ("the '329 application"), the contents of which is incorporated by reference herein in its entirety.

The adapter assembly 100 will now be described with reference to FIGS. 3-20. Referring initially to FIG. 3, the adapter assembly 100 includes a proximal end 102 configured for operable connection to the connecting portion 18a (FIG. 1) of the surgical device 10 (FIG. 1) and a distal end 104 configured for operable connection to the extension assembly 200 (FIG. 1).

Turning to FIGS. 3-5, from the proximal end 102 to the distal end 104 of the adapter assembly 100, the adapter assembly 100 includes a drive coupling assembly 110, a drive transfer assembly 130 operably connected to the drive coupling assembly 110, a first pusher assembly 160 operably connected to the drive transfer assembly 130, and a second pusher assembly 180 operably connected to the drive transfer assembly 130. Each of the drive transfer assembly 130 and the first and second pusher assemblies 160, 180 are operably maintained within an outer sleeve 106 (FIG. 3). As will be described in further detail below, a shaft 108 (FIG. 3) extends longitudinally through the adapter assembly 100 and is operably connected to the drive transfer assembly 130.

With reference to FIGS. 5-9, the drive coupling assembly 110 has a cylindrical profile and is configured to selectively secure the adapter assembly 100 to the surgical device 10 (FIG. 1). The drive coupling assembly 110 includes a connector housing 112 and a connector extension 114 fixedly connected to the connector housing 112 by a mounting plate 113. The connector housing 112 and the connector extension 114 operate to rotatably support a first rotatable proximal drive shaft 116, a second rotatable proximal drive shaft 118, and a third rotatable proximal drive shaft 120. The connector housing 112 and the connector extension 114 of the drive coupling assembly 110 also rotatably support the first, second, and third connector sleeves 122, 124, and 126, respectively. Each of the connector sleeves 122, 124, 126 is configured to mate with the respective first, second, and third drive connectors (not shown) of surgical device 10 (FIG. 1). Each of the connector sleeves 122, 124, 126 is further configured to mate with a proximal end 116a, 118a, 120a of the respective first, second and third proximal drive shafts 116, 118, 120.

The drive coupling assembly 110 also includes first, second and third biasing members 122a, 124a and 126a disposed distally of the respective first, second and third connector sleeves 122, 124, 126. Each of the biasing members 122a, 124a and 126a is disposed about the respective first, second and third rotatable proximal drive shafts 122, 124 and 126 to help maintain the connector sleeves 122, 124, and 126 engaged with the distal end of the respective rotatable drive connectors (not shown) of the surgical device 10 when the adapter assembly 100 is connected to the surgical device 10. In particular, the first, second, and third biasing members 122a, 124a, and 126a function to bias the respective connector sleeves 122, 124, and 126 in a proximal direction.

For a detailed description of an exemplary drive coupling assembly, please refer to the '329 application, the contents of which were previously incorporated by reference herein.

With reference to FIGS. 9-13, the drive transfer assembly 130 has a cylindrical profile and operably connects the distal ends of the first, second, and third rotatable proximal drive shafts 116, 118, and 120 to the shaft 108, the first pusher assembly 160, and the second pusher assembly 180, respectively. The drive transfer assembly 130 includes a support plate 132 (FIGS. 11 and 12) secured to a proximal end of the connector housing 112 and a drive transfer housing 134 positioned adjacent the support plate 132. The support plate 132 and the housing 134 operate to rotatably support a first rotatable distal drive shaft 136, a second rotatable distal drive shaft 138 and a drive member 140.

The first and second rotatable distal drive shafts 136 and 138 are each operably connected to the respective first and second rotatable proximal drive shafts 116 and 118 of the drive coupling assembly 110 by a pair of gears. In particular, the distal ends of each of the first and second rotatable proximal drive shaft 116 and 118 include a geared portion 142a and 144a, respectively, which engages a proximal drive gear 142b and 144b on a proximal end of the respective first and second distal drive shafts 136 and 138. As shown, each of the respective paired geared portions and proximal drive gears 142a, 142b and 144a, 144b are the same size to provide a 1:1 gear ratio between the respective first and second rotatable proximal and distal drive shafts 116, 136 and 118, 138. In this manner, the respective first and second rotatable proximal and distal drive shafts 116, 136 and 118, 138 rotate at the same speed. However, it is envisioned that either or both of the paired geared portions and proximal drive gears may be of different sizes to alter the gear ratio between the first and second rotatable proximal and distal drive shafts 116, 136 and 118, 138.

Figure 17:
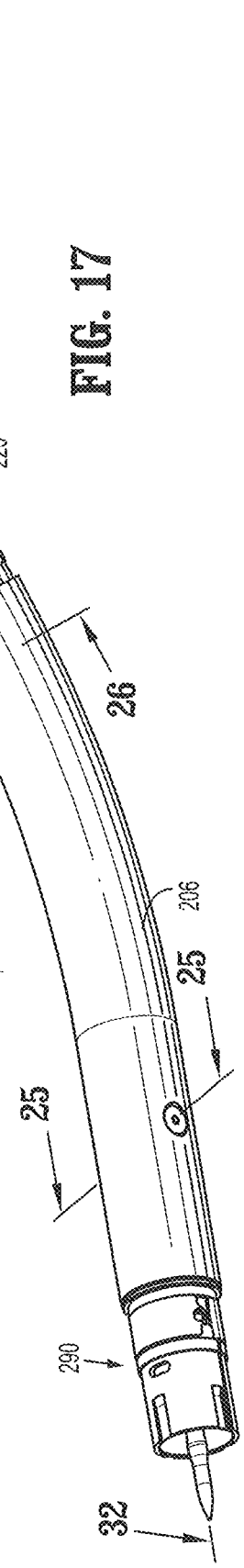
FIG. 17 is a perspective side view of the extension assembly of FIG. 1.
Figure 21:
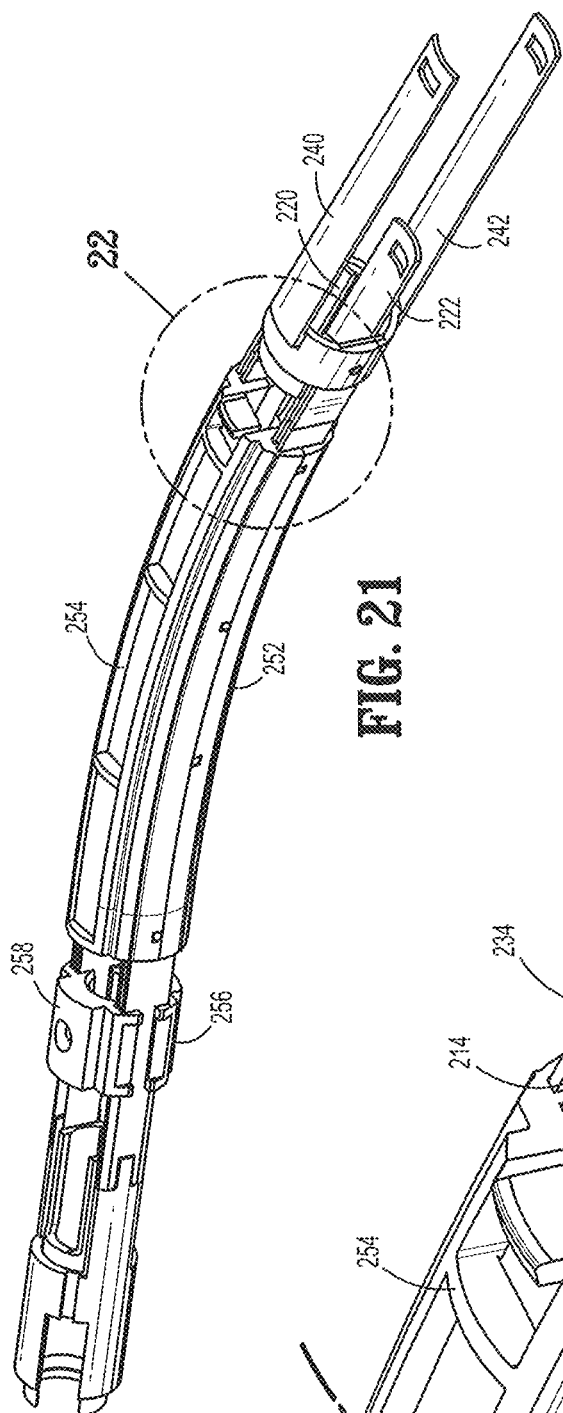
FIG. 21 is a perspective side view of the inner and outer flexible band assemblies and frame assembly of FIG. 20.
Figure 22:
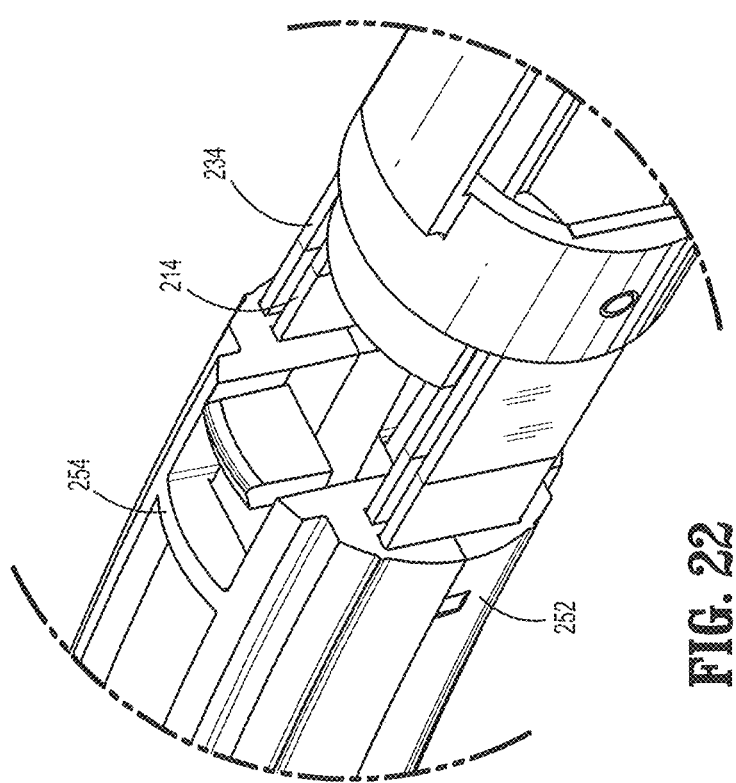
FIG. 22 is an enlarged view of the indicated area of detail of FIG. 21.
Figure 25:
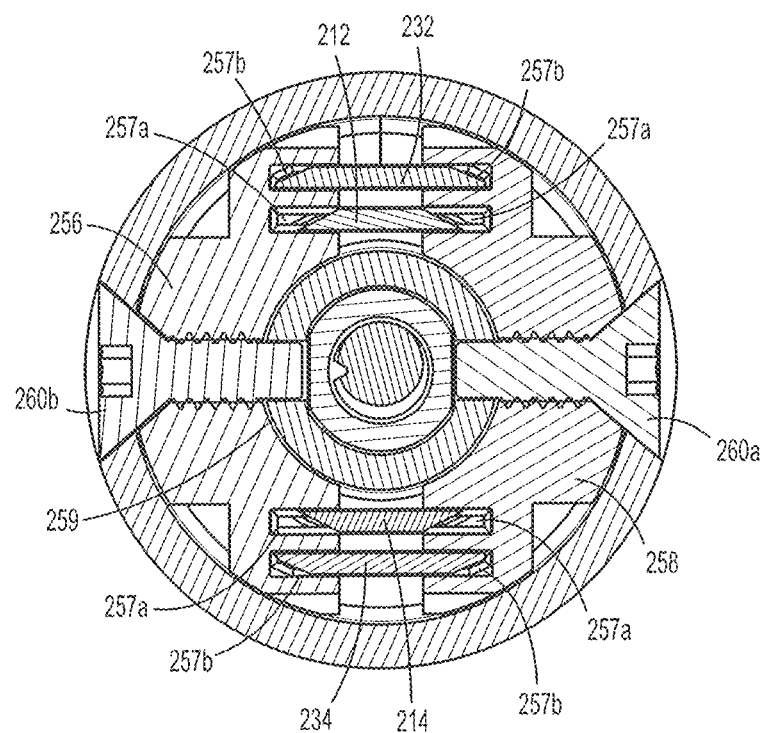
FIG. 25 is a cross-sectional end view taken along line 25-25 of FIG. 17.

A distal end of the third proximal drive shaft 120 of the drive coupling assembly 110 includes a geared portion 146a that engages a geared portion 146b formed on a proximal end of the drive member 140 of the drive transfer assembly 130. The size of the geared portion 146a on the third proximal drive shaft 120 and the geared portion 146b on the drive member 140 are the same size to provide a 1:1 gear ratio between the third proximal drive shaft 120 and the drive member 140. In this manner, the third proximal drive shaft 120 and the drive member 140 rotate at the same speed. However, it is envisioned that either or both of the geared portions 146a, 146b may be of different sizes to alter the gear ratio between the third proximal drive shaft 120 and the drive member 140. A distal end of the drive member 140 defines a socket 145 that receives a proximal end 108a of the shaft 108. Alternatively, the socket 145 may be configured to operably engage a proximal end 208a of a drive shaft (FIG. 17) of an extension assembly 200 (FIG. 17).

The drive transfer assembly 130 also includes a drive connector 148 (FIG. 11) operably connecting the first rotatable distal drive shaft 136 to the first pusher assembly 160 and a tubular connector 150 operably connecting the second rotatable distal drive shaft 138 to the second pusher assembly 180. In particular, a distal end of the first rotatable distal drive shaft 136 includes a geared portion 152a that engages a geared portion 152b of the drive connector 148. A distal end of the second rotatable distal drive shaft 138 includes a geared portion 154a that engages a drive gear 154b secured to a distal end of the tubular connector 150.

As shown, the geared portion 152a of the first rotatable distal drive shaft 136 is smaller than the geared portion 152b of the drive connector 148 to provide a gear ratio of greater than 1:1 between the first rotatable distal drive shaft 136 and the drive connector 148. In this manner, the drive connector 148 rotates at a slower speed than the first rotatable distal drive shaft 136. Similarly, the geared portion 154a of the second rotatable distal drive shaft 138 is smaller than the drive gear 154b on the tubular connector 150 to provide a gear ratio of greater than 1:1 between the second rotatable distal drive shaft 138 and the drive connector 148. In this manner, the tubular connector 150 rotates at a slower speed than the second rotatable distal drive shaft 138. However, it is envisioned that each of the paired geared portions 152a, 152b, and the geared portion 154a and the drive gear 154b may be the same size to provide a gear ratio of 1:1 between the respective first rotatable distal drive shaft 136 and the drive connector 148 and between the second rotatable distal drive shaft 138 and the tubular connector 150.

With particular reference to FIGS. 9-13, the first pusher assembly 160 includes proximal and distal housing sections 162, 164 (FIG. 11), a planetary gear assembly 166 operably mounted within the proximal housing section 162, a screw member 168 (FIG. 11) operably connected to the planetary gear assembly 166 and rotatably supported within the distal housing section 164, and a pusher member 170 (FIG. 11) operably connected to the screw member 168 and slidably disposed within the distal housing section 164. The proximal housing section 162 includes a pair of longitudinal flanges 162a (FIG. 4; only one shown) and the distal housing section 164 includes a pair of longitudinally flattened portions 164a. Each of the flanges 162a and the flattened portions 164a of the respective proximal and distal housing sections 162, 164 engage an inner surface of the sleeve 106 to prevent rotation of the respective proximal housing section 162 and the distal housing section 164 relative to the sleeve 106 during operation of the surgical device 10.

Figure 10:
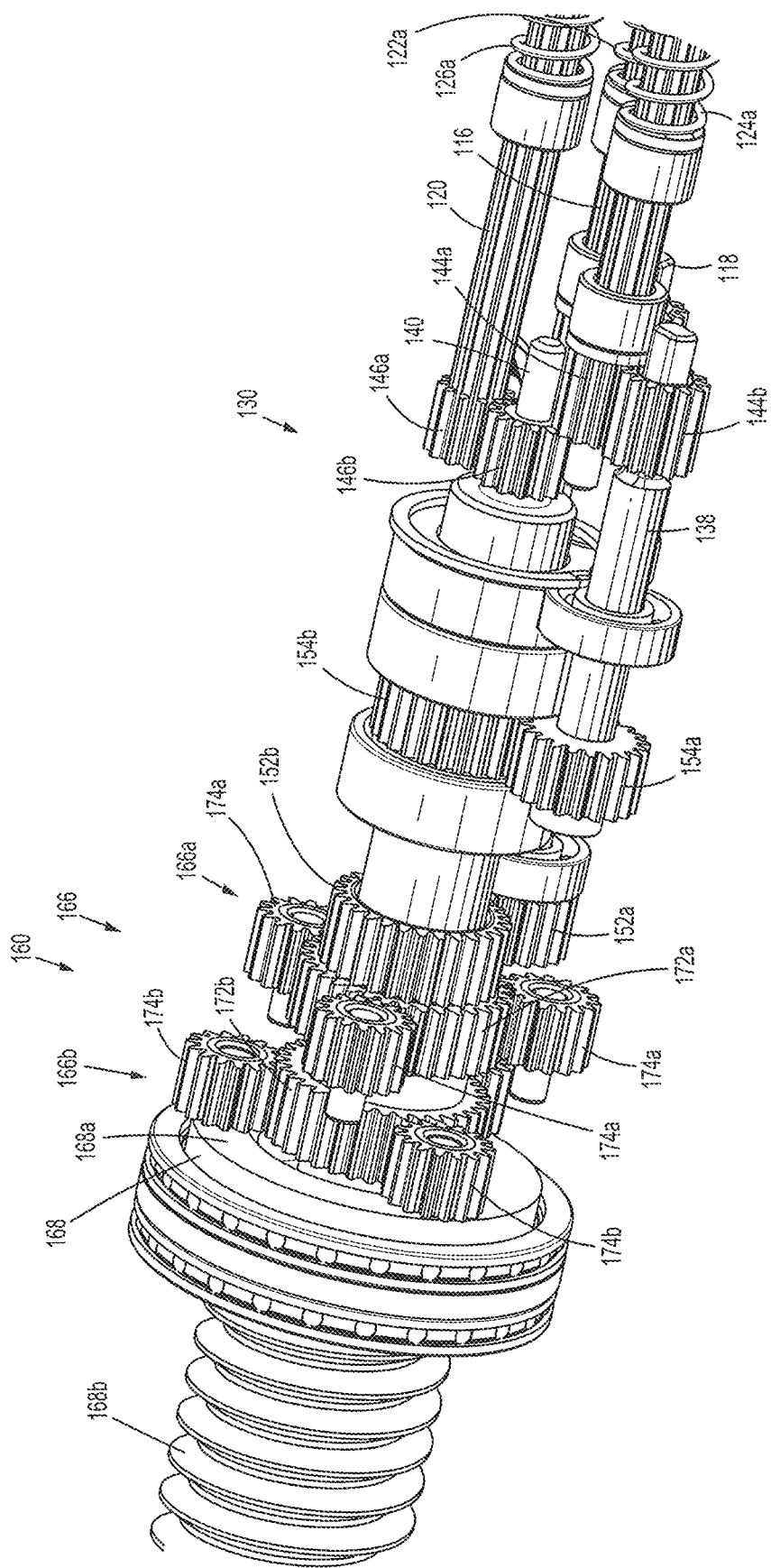
FIG. 10 is an enlarged view of the indicated area of detail of FIG. 9.
Figure 11:
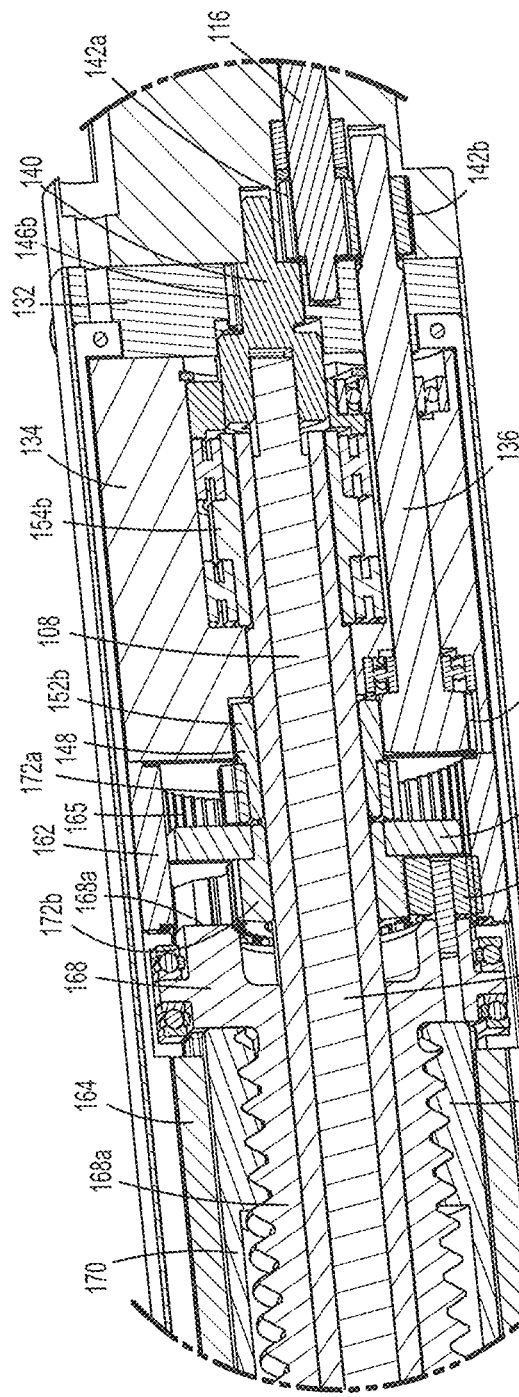
FIG. 11 is an enlarged view of the indicated area of detail of FIG. 6.

The planetary gear assembly 166 includes first and second planetary gear systems 166a, 166b (FIG. 10). The first planetary gear system 166a of the first pusher assembly 160 includes a central drive gear 172a mounted on a distal end of the drive connector 148 of the drive transfer assembly 130 and a plurality of planetary gears 174a rotatably mounted to a rotatable support ring 176.

Each of the planetary gears 174a engages the central drive gear 172a and a toothed inner surface 165 of the proximal housing section 162. As central drive gear 172a rotates in a first direction, i.e., clockwise, each of the planetary gears 174a rotates in a second direction, i.e., counter-clockwise. As each of the planetary gears 174a rotates in the second direction, engagement of the planetary gears 174a with the toothed inner surface 165 of the distal housing section 162 causes the rotatable support ring 176 to rotate in the first direction. Conversely, rotation of the central drive gear 172a in the second direction causes rotation of each of the planetary gears 174a in the first direction thereby causing rotation of the rotatable support ring 176 in the second direction. The configuration of the first planetary gear system 166a provides a reduction in the gear ratio. In this manner, the speed of rotation of the rotatable support ring 174 is less than the speed of rotation of the central drive gear 172a.

The second planetary gear system 166b of the first pusher assembly 160 includes a central drive gear 172b securely affixed to the rotatable support ring 176 and a plurality of planetary gears 174b rotatably mounted to a proximal end surface 168a of the screw member 168. Each of the planetary gears 174b engages the central drive gear 172b and the toothed inner surface 165 of the proximal housing section 162. As the rotatable support ring 176 of the first planetary gear system 166a rotates in the first direction thereby causing the central drive gear 172b to also rotate in the first direction, each of the planetary gears 174b rotates in the second direction. As each of the planetary gears 174b rotates in the second direction, engagement of the planetary gears 174b with the toothed inner surface 165 of the proximal housing section 162 causes the screw member 168 to rotate in the first direction. Conversely, rotation of the central drive gear 172b in the second direction causes rotation of each of the planetary gears 174b in the first direction, thereby causing the screw member 168 to rotate in the second direction. The configuration of the second planetary gear system 166b provides a reduction in the gear ratio. In this manner, the speed of rotation of the screw member 168 is less than the speed of rotation of the central drive gear 172b.

The first and second planetary gear systems 166a, 166b operate in unison to provide a reduction in the gear ratio between the first rotatable proximal drive shaft 116 and the screw member 168. In this manner, the reduction in the speed of rotation of the screw member 168 relative to the drive connector 148 is a product of the reduction provided by the first and second planetary gear systems 166a, 166b.

The screw member 168 is rotatably supported within the proximal housing portion 162 and includes a threaded distal end 168b that operably engages a threaded inner surface 170a of the pusher member 170. As the screw member 168 is rotated in the first direction, engagement of the threaded distal end 168b of the screw member 168 with the threaded inner surface 170a of the pusher member 170 causes longitudinal advancement of the pusher member 170, as indicated by arrows "A" in FIG. 12. Conversely, rotation of the screw member 168 in the second direction causes retraction of the pusher member 170.

The pusher member 170 includes a pair of tabs 178 formed on a distal end thereof for engaging the connector extensions 240, 242 (FIG. 19) of the outer flexible band assembly 230 (FIG. 19) of the extension assembly 200 (FIG. 17). Although shown as tabs 178, it is envisioned that the pusher member 170 may include any structure suitable for selectively engaging the connector extensions 240, 242 of the outer flexible band 230 of the extension assembly 200.

Figure 16:
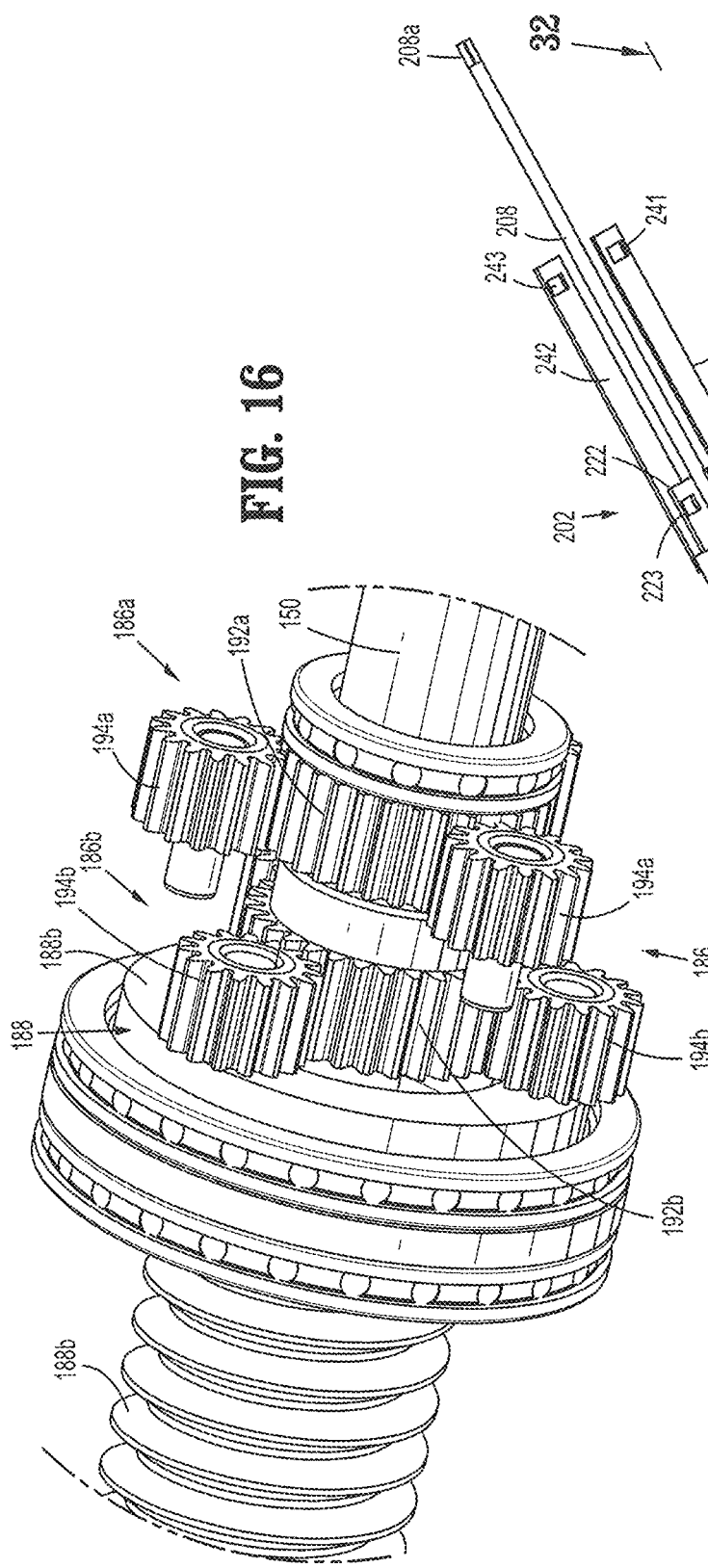
FIG. 16 is an enlarged view of the indicated area of detail of FIG. 9.

With particular reference now to FIGS. 14-16, the second pusher assembly 180 is substantially similar to the first pusher assembly 160, and includes proximal and distal housing sections 182, 184, a planetary gear assembly 186 operably mounted within the proximal housing section 182, a screw member 188 operably connected to the planetary gear assembly 186 and rotatably supported within the distal housing section 184, and a pusher member 190 operably connected to the screw member 188 and slidably disposed within the distal housing section 184. Each of the proximal housing section 182 and the distal housing section 184 includes a pair of longitudinal flanges 182a, 184a (FIG. 4; only one shown), respectively, engaging an inner surface of the sleeve 106 of the adapter assembly 100 to prevent rotation of the respective proximal housing section 182 and the distal housing section 184 relative to the sleeve 106 during operation of the surgical device 10.

The planetary gear assembly 186 includes first and second planetary gear systems 186a, 186b (FIG. 16). The first planetary gear system 186a of the second pusher assembly 180 includes a central drive gear 192a mounted on a distal end of the tubular connector 150 of the drive transfer assembly 130 and a plurality of planetary gears 194*a* rotatably mounted to a rotatable support ring 196.

Each of the planetary gears 194*a* engages the central drive gear 192*a* and a toothed inner surface 185 of the proximal housing section 182. As central drive gear 192*a* rotates in a first direction, i.e., clockwise, each of the planetary gears 194*a* rotates in a second direction, i.e., counter-clockwise. As each of the planetary gears 194*a* rotates in the second direction, engagement of the planetary gears 194*a* with toothed inner surface 185 of the distal housing section 182 causes the rotatable support ring 196 to rotate in the first direction. Conversely, rotation of the central drive gear 192*a* in the second direction causes rotation of each of the planetary gears 194*a* in the first direction thereby causing rotation of the rotatable support ring 196 in the second direction. The configuration of the first planetary gear system 186*a* provides a reduction in the gear ratio. In this manner, the speed of rotation of the rotatable support ring 194 is less than the speed of rotation of the central drive gear 190*a*.

The second planetary gear system 186*b* of the second pusher assembly 180 includes a central drive gear 192*b* securely affixed to the rotatable support ring 196 and a plurality of planetary gears 194*b* rotatably mounted to a proximal end surface 188*a* of the screw member 188. Each of the planetary gears 194*b* engages the central drive gear 192*b* and the toothed inner surface 185 of the proximal housing section 182. As the rotatable support ring 196 of the first planetary gear system 186*a* rotates in the first direction thereby causing the central drive gear 192*b* to also rotate in the first direction, each of the planetary gears 174*b* rotates in the second direction. As each of the planetary gears 194*b* rotates in the second direction, engagement of the planetary gears 194*b* with the toothed inner surface 185 of the proximal housing section 182 causes the screw member 188 to rotate in the first direction. Conversely, rotation of the central drive gear 192*b* in the second direction causes rotation of each of the planetary gears 194*b* in the first direction, thereby causing the screw member 198 to rotate in the second direction. The configuration of the second planetary gear system 186*b* provides a reduction in the gear ratio. In this manner, the speed of rotation of the screw member 188 is less than the speed of rotation of the central drive gear 182*b*. The first and second planetary gear systems 186*a*, 186*b* operate in unison to provide a reduction in the gear ratio between the second rotatable proximal drive shaft 118 and the screw member 188. In this manner, the reduction in the speed of rotation of the screw member 188 relative to the tubular connector 150 is a product of the reduction provided by the first and second planetary gear systems 186*a*, 186*b*.

The screw member 188 is rotatably supported within the proximal housing portion 182 and includes a threaded distal end 188*b* that operably engages a threaded inner surface 190*a* of the pusher member 190. As the screw member 188 is rotated in the first direction, engagement of the threaded distal end 188*b* of the screw member 188 with the threaded inner surface 190*a* of the pusher member 190 causes longitudinal advancement of the pusher member 190. Conversely, rotation of the screw member 188 in the second direction causes retraction of the pusher member 190. The pusher member 190 includes a pair of longitudinal flanges 191 (FIG. 5; only one shown) that engage the distal housing section 184 of the second pusher assembly 180 for preventing rotation of the pusher member 190 relative to the distal housing section 184.

The pusher member 190 includes a pair of tabs 198 formed on a distal end thereof for engaging the connector extensions 220, 224 (FIG. 18) of the inner flexible band assembly 220 (FIG. 18) of the extension assembly 200 (FIG. 17). Although shown as tabs 198, it is envisioned that the pusher member 190 may include any structure suitable for selectively engaging the connector extensions 240, 242 of the outer flexible band 230 of the extension assembly 200.

The extension assembly 200 for operably connecting the adapter assembly 100 (FIG. 3) with a circular loading unit, e.g. the loading unit 40 (FIG. 34) and an anvil assembly, e.g., the anvil assembly 50 (FIG. 34) will be described with reference now to FIGS. 17-34. In particular, a proximal end 202 of the extension assembly 200 operably connects with the distal end 104 (FIG. 3) of the adapter assembly 100 (FIG. 3) and a distal end 204 of the extension assembly 200 operably connects with the loading unit 40 and the anvil assembly 50. As shown, the extension assembly 200 provides a slight curvature between the proximal and distal ends 202, 204. In an alternative embodiment, the extension assembly 200 may be straight or may include a greater curvature. Although the extension assembly 200 will be shown and described as being used to connect the loading unit 40 and the anvil assembly 50 to the adapter assembly 100 (FIG. 3), it is envisioned that the aspects of the present disclosure may be modified for use with various loading units, anvil assemblies, and adapter assemblies. Exemplary loading units and anvil assemblies are described in commonly owned U.S. Pat. No. 8,590,763 and U.S. patent application Ser. Nos. 14/056,301 and 14/149,355, the contents of each being incorporated herein by reference in their entirety.

The extension assembly 200 includes an inner flexible band assembly 210 (FIG. 18), an outer flexible band assembly 230 (FIG. 19) slidably disposed about the inner flexible band assembly 210, a frame assembly 250 (FIG. 20) for supporting the inner and outer flexible band assemblies 210, 230, a trocar assembly 270 (FIG. 29) operably received through the inner and outer flexible band assemblies 210, 230, and a connector assembly 290 for securing the loading unit 40 (FIG. 34) to the extension assembly 200. An outer sleeve 206 (FIG. 17) is received about the frame assembly 250 and the trocar assembly 270 and the inner and outer flexible band assemblies 210, 230 are slidably received through the outer sleeve 206. As will be described in further detail below, the extension assembly 200 may include a drive shaft 208 operably connected to the trocar assembly 270 and extending through the proximal end 202 of the extension assembly 200.

With reference to FIG. 18, the inner flexible band assembly 210 includes first and second inner flexible bands 212, 214, a support ring 216, a support base 218, and first and second connection extensions 220, 222. The proximal ends 212*a*, 214*a* of the respective first and second inner flexible bands 212, 214 are laterally spaced apart and securely attached to the support ring 216. The distal ends 212*b*, 214*b* of the first and second inner flexible bands 212, 214 are laterally spaced apart and securely attached to a proximal end 218*a* of the support base 218. Each of the first and second inner flexible bands 212, 214 may be attached to the support ring 216 and/or the support base 218 in any suitable manner, including, for example, by press-fitting, welding, adhesives, and/or with mechanical fasteners. As will be described in further detail below, the inner flexible band assembly 210 is configured to be slidably received about the trocar assembly 270 (FIG. 28) and within the outer flexible band assembly 230 (FIG. 19) and the outer sleeve 206 (FIG. 17).

The first and second connection extensions 220, 222 of the inner flexible band assembly 210 extend proximally from the support ring 216 and operably connect the inner flexible band assembly 210 with the pusher member 190 (FIG. 15) of the second pusher assembly 180 (FIG. 15) of the adapter assembly 100 (FIG. 3). In particular, each of the first and second connection extensions 220, 222 define openings 221, 223 configured to receive tabs 198 (FIG. 15) of the pusher member 190 (FIG. 15) of the second pusher assembly 180. Receipt of the tabs 198 of the pusher member 190 within the openings 221, 223 of the respective first and second extensions 220, 222 secure the inner flexible band assembly 210 of the extension assembly 200 with the second pusher assembly 180 of the adapter assembly 100. The first and second connection extensions 220, 222 may be integrally formed with the support ring 216, or attached thereto in any suitable manner.

The support base 218 extends distally from the inner flexible bands 212, 214 and is configured to selectively connect the extension assembly 200 with the loading unit 40 (FIG. 34). Specifically, a distal end 218b of the support base 218 includes a flange 224 for operable engagement with an axially movable assembly (not shown) of the loading unit 40 (FIG. 34). In one embodiment, the flange 224 is configured for connection with a knife assembly (not shown) of the loading unit 40 (FIG. 34).

With reference now to FIG. 19, the outer flexible band assembly 230 is substantially similar to the inner flexible band assembly 210 and includes first and second flexible bands 232, 234 laterally spaced and connected on proximal ends 232a, 234a to a support ring 236 and on distal ends 232b, 234b to a proximal end 238a of a support base 238. Each of the first and second outer flexible bands 232, 234 may be attached to the support ring 236 and the support base 238 in any suitable manner, including, for example, by press-fitting, welding, adhesives, and/or with mechanical fasteners. As will be described in further detail below, the outer flexible band assembly 230 is configured to receive the trocar assembly 270 (FIG. 29) therethrough.

The first and second connection extensions 240, 242 of the outer flexible band assembly 230 extend proximally from the support ring 236 and operably connect the outer flexible band assembly 230 with the pusher member 170 (FIG. 12) of the first pusher assembly 160 (FIG. 12) of the adapter assembly 100 (FIG. 1). In particular, each of the first and second connection extensions 240, 242 define openings 241, 243 configured to receive the tabs 178 (FIG. 12) of the pusher member 170 of the first pusher assembly 180. Receipt of the tabs 178 of the pusher member 170 within the openings 241, 243 of the respective first and second extensions 240, 242 secures the outer flexible band assembly 230 of the extension assembly 200 with the first pusher assembly 180 of the adapter assembly 100. The first and second connection extensions 240, 242 may be integrally formed with the support ring 236, or attached thereto in any suitable manner.

The support base 238 extends distally from the outer flexible bands 232, 234 and is configured to selectively connect the extension assembly 200 with the loading unit 40 (FIG. 34). Specifically, a distal end 238b of the support base 238 includes a flange 244 for operable engagement with an axially movable assembly (not shown) of a loading unit (not shown). In one embodiment, the flange 244 is configured for connection with a staple pusher assembly (not shown) of the loading unit 40 (FIG. 34).

With reference now to FIGS. 20-26, the frame assembly 250 includes first and second proximal spacer members 252, 254, and first and second distal spacer members 256, 258. When secured together, the first and second proximal spacer members 252, 254 define a pair of inner longitudinal slots 253a for slidably receiving the first and second flexible bands 212, 214 (FIG. 18) of the inner flexible band assembly 210 (FIG. 18) and a pair of outer longitudinal slots 253b for slidably receiving the first and second flexible bands 232, 234 (FIG. 19) of the outer flexible band assembly 230 (FIG. 19). The first and second proximal spacer members 252, 254 further define a longitudinal passage 255 for receipt of the trocar assembly 270.

In one embodiment, and as shown, the first and second proximal spacer members 252, 254 are formed of plastic and are secured together with a snap-fit arrangement. Alternatively, the first and second proximal spacer members 252, 254 may be formed of metal or other suitable material and may be secured together in any suitable manner, including by welding, adhesives, and/or using mechanical fasteners.

The first and second distal spacer members 256, 258 define a pair of inner slots 257a for slidably receiving the first and second flexible bands 212, 214 (FIG. 18) of the inner flexible band assembly 210 (FIG. 18) and a pair of outer slots 257b for slidably receiving the first and second flexible bands 232, 234 (FIG. 19) of the outer flexible band assembly 230 (FIG. 19). The first and second distal spacer members 256, 258 further define a longitudinal passage 259 for receipt of the trocar assembly 270.

Figure 26:
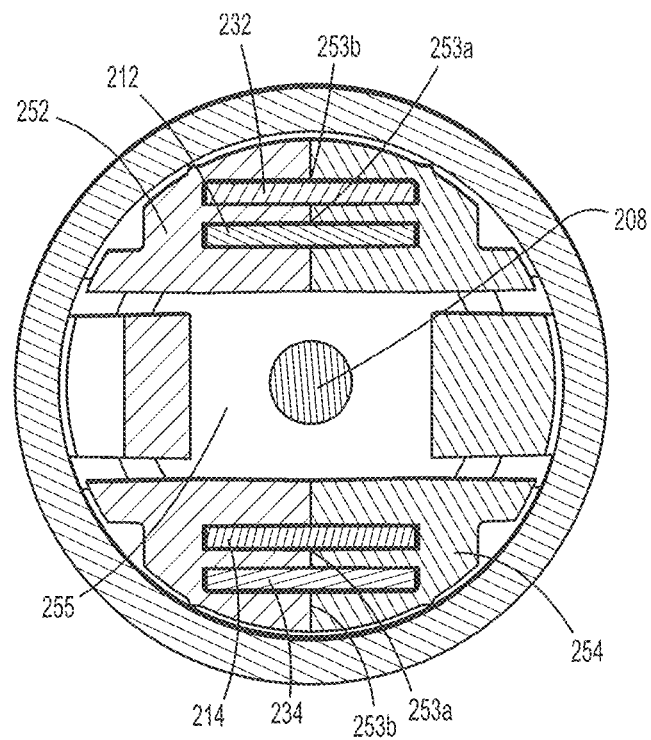
FIG. 26 is a cross-sectional end view taken along line 26-26 of FIG. 17.

In one embodiment, and as shown, each of the first and second distal spacer members 256, 258 are secured about the inner and outer flexible band assemblies 210, 230 and to the outer sleeve 206 (FIG. 17) by a pair of screws 260a, 260b (FIG. 26). Alternatively, the first and second distal spacer members 256, 258 may be secured together in any suitable manner, including by welding, adhesives, and/or using mechanical fasteners. The first and second distal spacer members 256, 258 may be formed of metal or any other suitable material.

Figure 27:
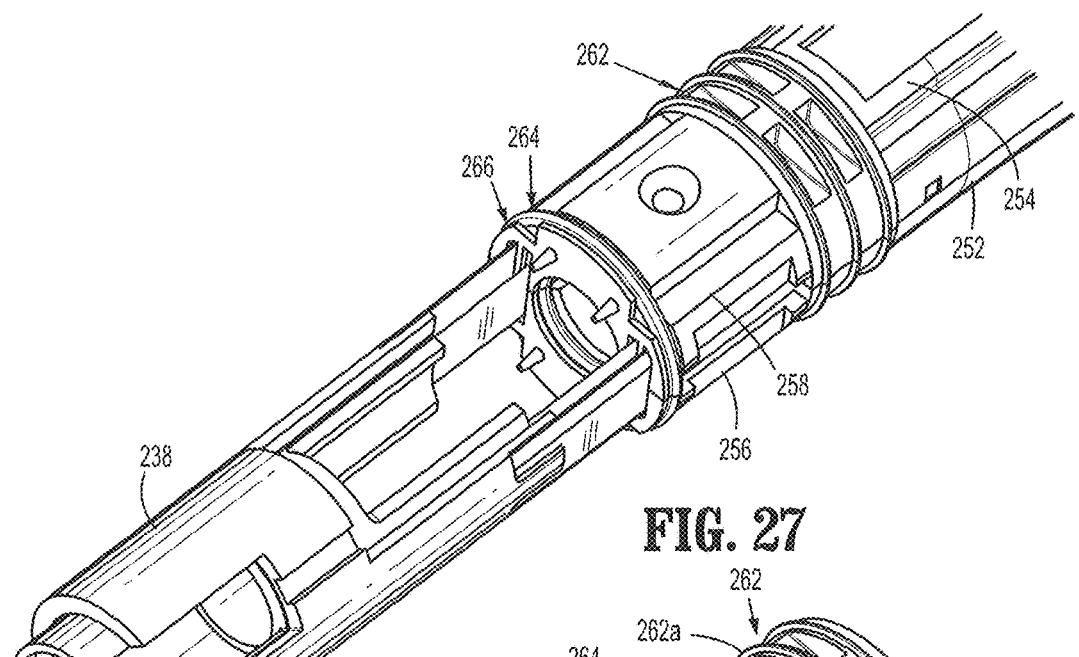
FIG. 27 is an enlarged perspective side view of a distal end of the inner and outer flexible band assemblies and frame assembly of FIG. 20 including a proximal seal member and first and second distal seal members.
Figure 28:
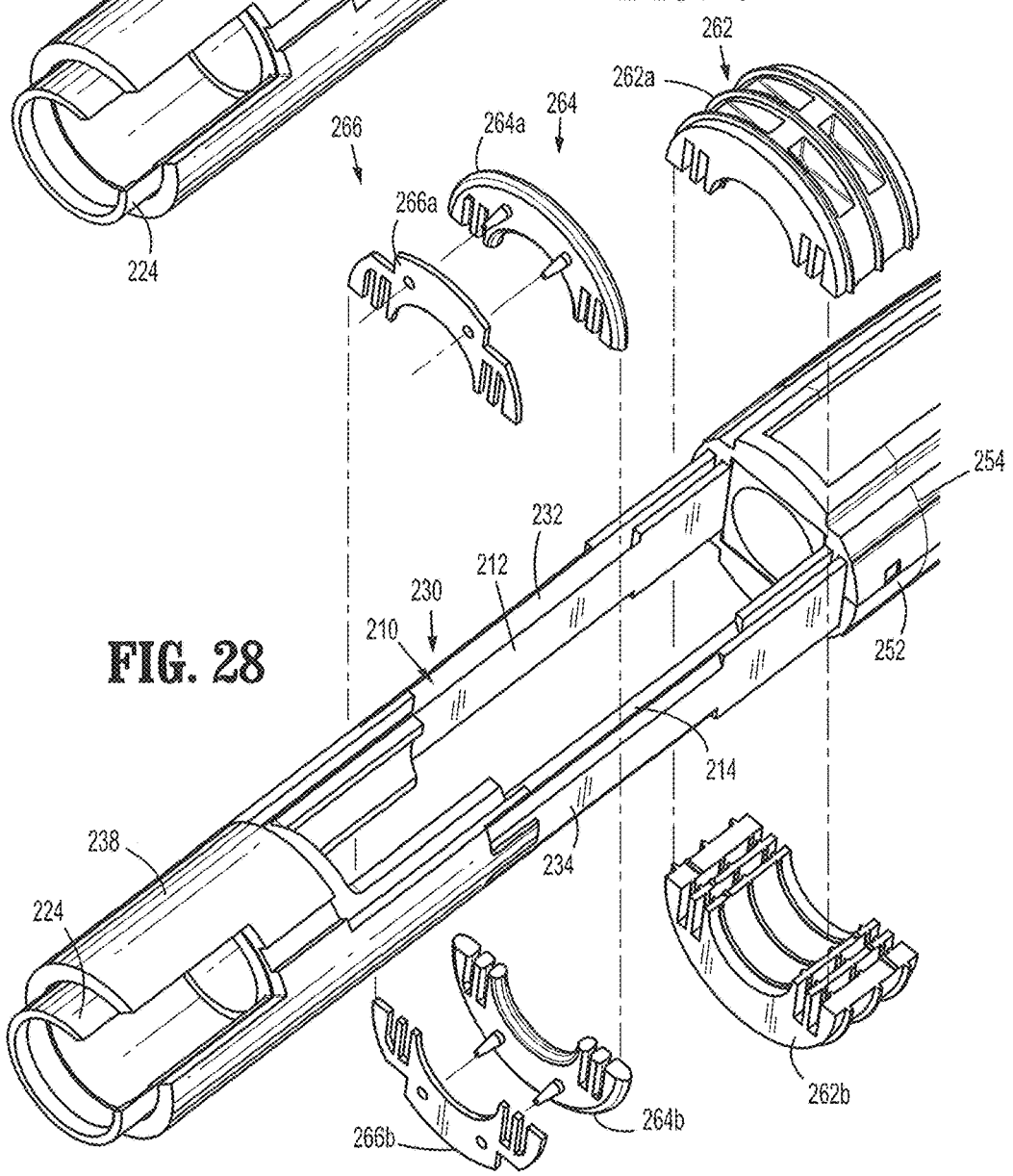
FIG. 28 is an exploded perspective view of the proximal seal member and first and second distal seal members of FIG. 27.
Figure 29:
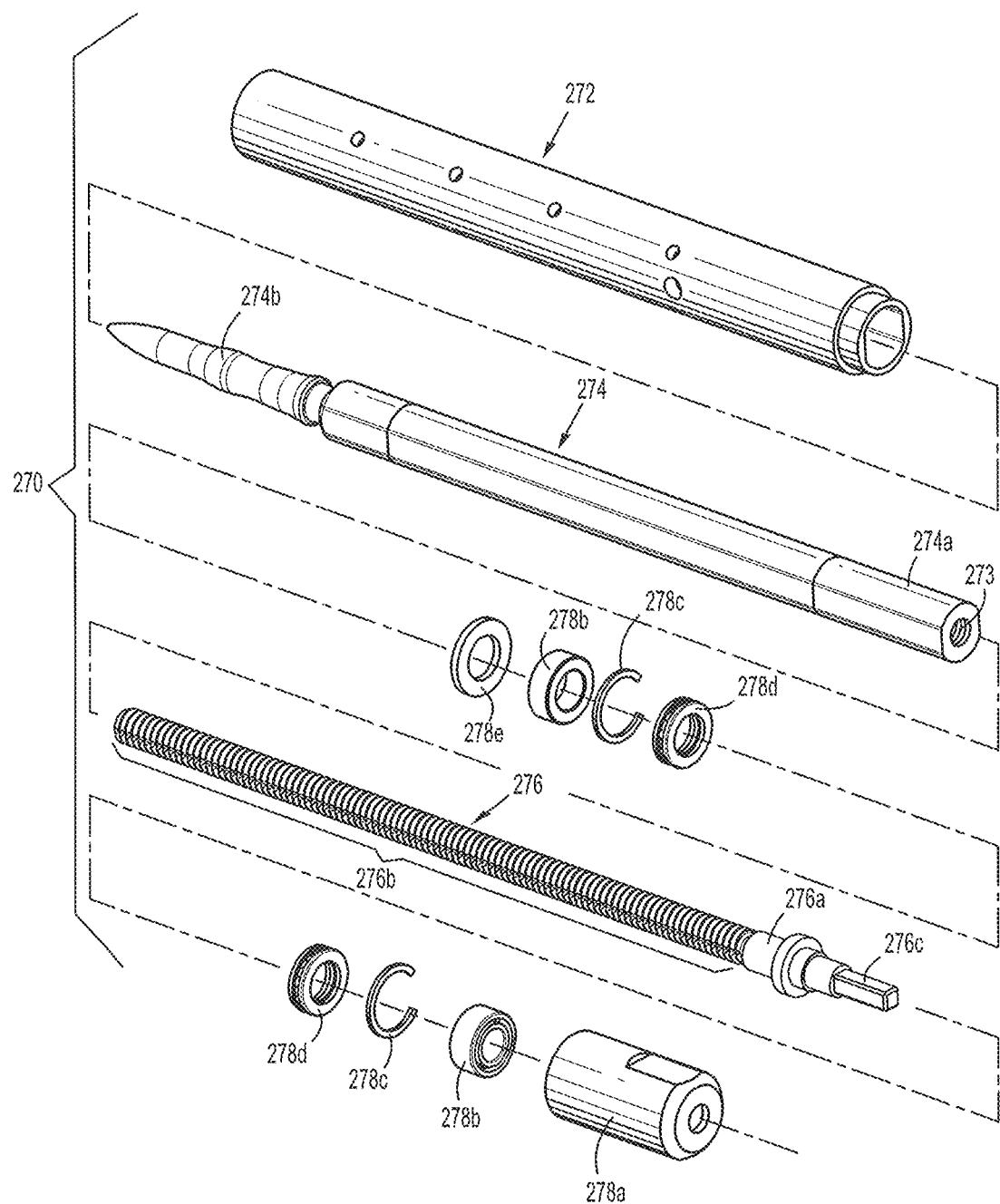
FIG. 29 is an exploded view of a trocar assembly of the extension assembly of FIG. 17.

With reference now to FIGS. 27 and 28, the frame assembly 250 further includes a proximal seal member 262 and first and second distal seal members 264, 266. Each of the proximal seal member 262 and the first and second distal seal members 264, 266 include seals halves 262a, 262b, 264a, 264b, 266a, 266b, respectively. The proximal seal member 262 is received between the first and second proximal spacer members 252, 254 and the first and second distal spacer members 256, 258. The first half 264a of the first distal seal member 264 is secured to the first half 266a of the second distal seal member 266 and the second half 264b of the first distal seal member 264 is secured to the second half 266b of the second distal seal member 266. The proximal seal member 262 and the first and second distal seal members 264, 266 engage the outer sleeve 206 (FIG. 17), the inner and outer flexible bands 212, 214, 232, 234 of the respective inner and outer flexible band assemblies 210, 230 and the trocar assembly 270 (FIG. 28) in a sealing manner. In this manner, the proximal seal member 262 and the first and second distal seal members 264, 266 operate to provide a fluid tight seal between the distal end 204 and the proximal end 202 of the extension assembly 200.

With reference to FIGS. 29-32, the trocar assembly 270 of the extension assembly 200 includes an outer housing 272, a trocar member 274 slidably disposed within the tubular outer housing 272, and a drive screw 276 operably received within the trocar member 274 for axially moving the trocar member 274 relative to the tubular housing 272. In particular, the trocar member 274 includes a proximal end 274a having an inner threaded portion 273 which engages a threaded distal portion 276b of the drive screw 276. As the drive screw 276 is rotated within the trocar member 274, engagement of the inner threaded portion 273 of the trocar member 274 with the threaded distal portion 276b of the drive screw 276 causes longitudinal movement of the trocar member 274 within the outer housing 272 of the trocar assembly 270. Rotation of the drive screw 276 in a first direction causes longitudinal advancement of the trocar member 274 and rotation of the drive screw 276 in a second direction causes longitudinal retraction of the trocar member 274. A distal end 274b of the trocar member 274 is configured to selectively engage the anvil assembly 50 (FIG. 34).

A bearing assembly 278 is mounted to a proximal end 272a of the outer housing 272 of the trocar assembly 270 for rotatably supporting a proximal end 276a of the drive screw 276 relative to the outer housing 272 and the trocar member 274. The bearing assembly 278 includes a housing 278a, proximal and distal spacers 278b, proximal and distal retention clips 278c, proximal and distal bearings 278d, and a washer 278e. As shown, the proximal end 276a of the drive screw 276 includes a flange 276c for connection with a link assembly 280.

The link assembly 280 operably connects the transfer assembly 130 (FIG. 6) of the adapter assembly 100 with the trocar assembly 270 (FIG. 30) of the extension assembly 200. More particularly, the link assembly 280 transfers rotational energy from the drive member 140 (FIG. 6) of the transfer assembly 130 of the adapter assembly 100 through the curved outer tube 206 (FIG. 17) of the extension assembly 200 to the flange 276c (FIG. 29) on the proximal end 276a of the drive screw 276 of the trocar assembly 270 of the extension assembly 200.

Figure 12:
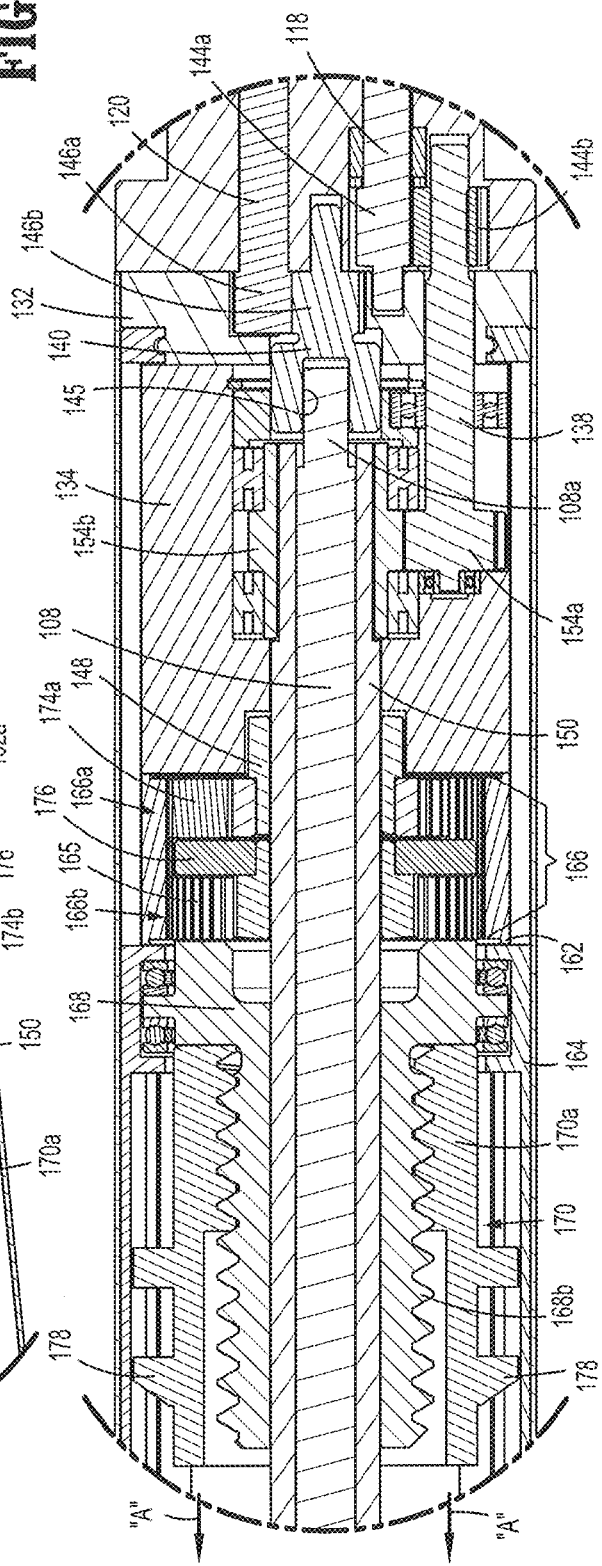
FIG. 12 is an enlarged view of the indicated area of detail of FIG. 7.
Figure 13:
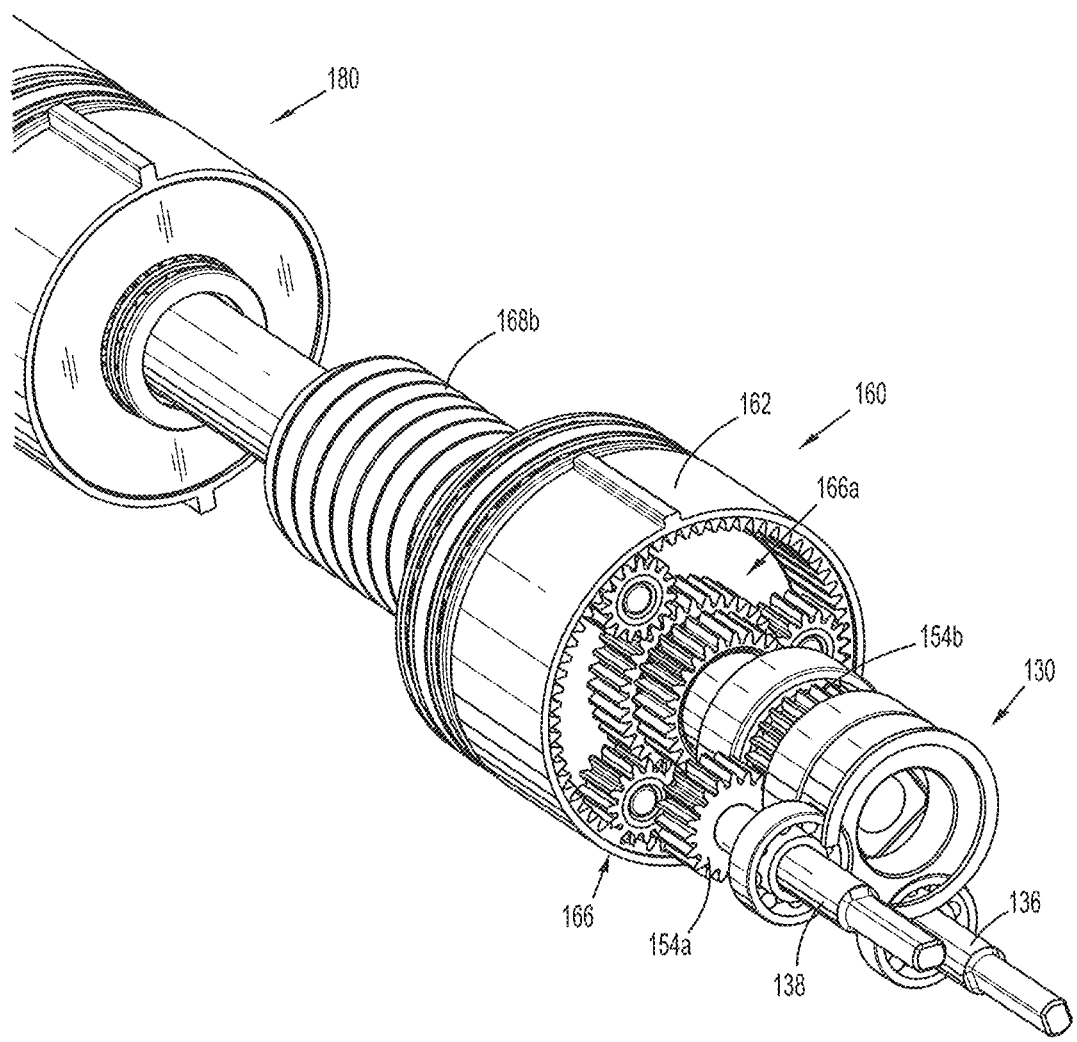
FIG. 13 is a perspective end view of the transfer assembly of FIG. 8.
Figure 32:
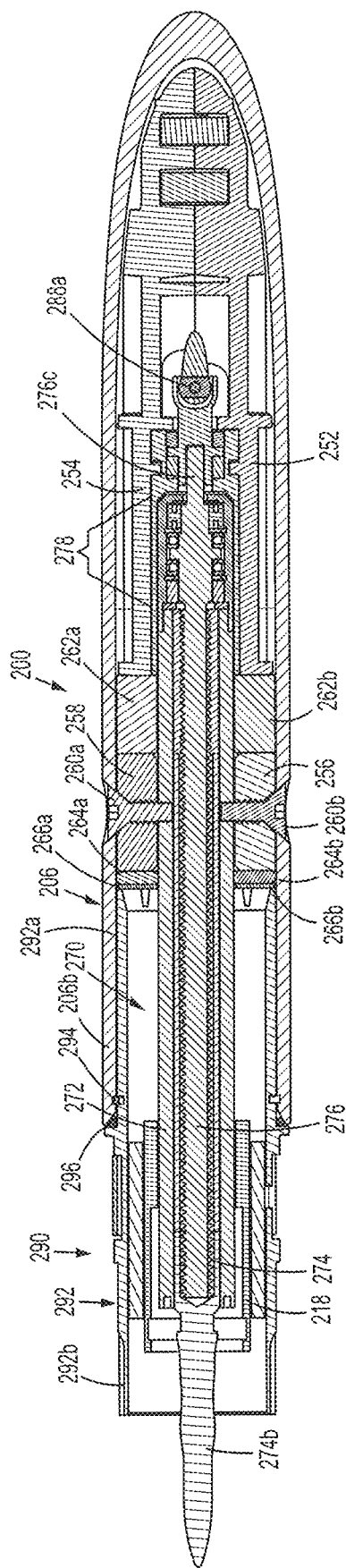
FIG. 32 is a cross-sectional top view taken along line 32-32 of FIG. 17.

With reference to FIGS. 29A and 29B, the link assembly 280 includes a coupling member 282, a first drive shaft 284, and a second drive shaft 286. A proximal end 282a of the coupling member 282 defines a recess 283a for receiving a distal end 284b of the first drive shaft 284. A distal end 282b of the coupling member 282 defines a recess 283a for operably receiving the flange 276c on the proximal end 276a of the drive screw 276. The coupling member 282 includes an annular flange 282c for rotatably receiving the coupling member 282 between the first and second proximal spacer members 252, 254 (FIG. 32). The proximal and distal ends 284a, 284b of the first drive shaft 284 define oversized openings 285a, 285b, respectively, for receiving pins 288a, 288b, respectively. A distal end 286b of the second drive shaft 286 defines a recess 287 for operably receiving the proximal end 284a of the drive shaft 284. A proximal end 286a of the drive shaft 286 includes a flange 286c for operable receipt within the socket 145 of the drive member 140 of the drive transfer assembly 130 of the adapter assembly 100 (FIG. 12).

With particular reference to FIG. 29B, the proximal end 284a of the first drive shaft 284 is operably received within the recess 287 in the distal end 286b of the second drive shaft 286. The distal end 284b of the first drive shaft 284 is pivotally secured within the recess 283a of the coupling member 282 by the pin 288a received through the oversized opening 285b in the distal end 284b of the first drive shaft 284. The proximal end 284a of the first drive shaft 284 is pivotally secured within the recess 287 in the distal end 286b of the second drive shaft 286 by the pin 288b received through the oversized opening 285a in the proximal end 284a of the first drive shaft 284. The recesses 283a and 287 of the coupling member 282 and the second drive shaft 286, respectively, and the oversized openings 285a, 285b of the first drive shaft 284 are configured to permit pivoting of the second drive shaft 286 relative to the first drive shaft 284 and pivoting of the first drive shaft 284 relative to the coupling member 282 as each of the first and second drive shafts 284, 286, and the coupling member 282 are rotated about their respective longitudinal axes to transfer rotational force from the transfer assembly 130 (FIG. 6) of the adapter assembly 100 to the trocar assembly 270 (FIG. 30) of the extension assembly 200.

Figure 33:
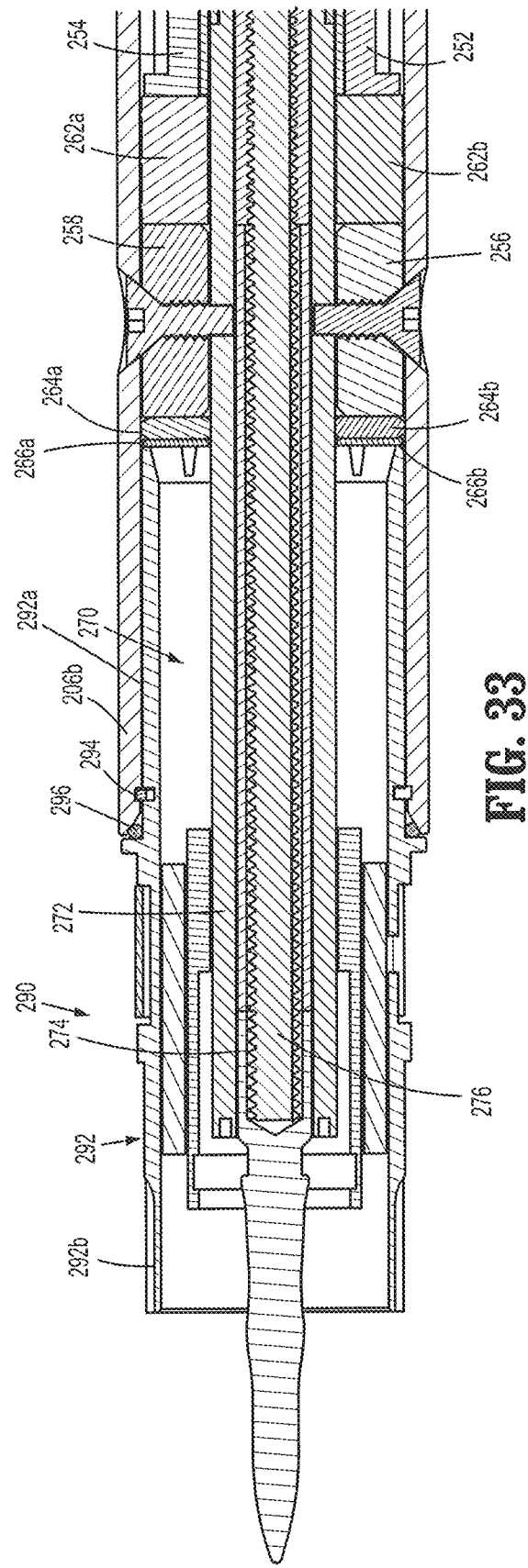
FIG. 33 is an enlarged cross-sectional view of the distal end of the extension assembly of FIG. 17.

With reference now to FIGS. 32 and 33, the connector assembly 290 of the extension assembly 200 includes a tubular connector 292 attached to a distal end 206b of the outer sleeve 206 and about distal ends of the inner and outer flexible assemblies 210, 230 (FIG. 26) and the trocar assembly 270. In particular, a proximal end 292a of the tubular connector 292 is received within and securely attached to the distal end 206b of the outer sleeve 206 by a retaining clip 294. An O-ring 296 forms a fluid tight seal between the tubular connector 292 of the connector assembly 290 and the outer sleeve 206. A distal end 292b of the tubular connector 292 is configured to selectively engage a proximal end of the loading unit 40 (FIG. 34). The distal end 292b of the tubular connector 292 engages the circular loading unit 40 with a snap-fit arrangement, bayonet coupling, or in another suitable manner.

With reference now to FIGS. 34 and 35, the extension assembly 200 is connected to the adapter assembly 100 by receiving the proximal end 202 (FIG. 17) of the extension assembly 200 within the distal end 104 of the adapter assembly 100. In particular, the first and second connection extensions 220, 222, 240, 242 of respective inner and outer flexible band assemblies 210, 230 are received within the sleeve 106 of the adapter assembly 100 such that tabs 178 of the pusher member 170 of the first pusher assembly 160 of the adapter assembly 100 are received within the openings 241, 243 of the respective first and second connection extensions 240, 242 of the outer flexible band assembly 230. In this manner, the outer flexible band assembly 230 is secured with the first pusher assembly 160. Additionally, the tabs 198 of the pusher member 190 of the second pusher assembly 180 of the adapter assembly 100 are received within the openings 221, 223 of the first and second connection extensions 221, 223 of the inner flexible band assembly 210 to secure the inner flexible band assembly 210 with the second pusher assembly 180.

As noted above, adapter assembly 100 may include a drive shaft 108 (FIG. 3) that extends from the distal end 104 of the adapter assembly 100. Prior to receipt of the proximal portion 202 of the extension assembly 200 within the distal end 104 of the extension assembly 100, the drive shaft 108 is removed from the adapter assembly 100. As the proximal portion 202 of the extension assembly 200 is received within the distal end 102 of the adapter assembly 100, the proximal end 286a (FIG. 17) of the second drive shaft 286 (FIG. 17) is received within the socket 145 of the drive member 140 of the drive transfer assembly 130 of the extension assembly 100 (FIG. 12).

After the extension assembly 200 is operably engaged with the adapter assembly 100, and the adapter assembly 100 is operably engaged with the surgical device 10 (FIG. 1), the loading unit 40 (FIG. 34) of the end effector 30 (FIG. 34) may be attached to the connector assembly 290 of the extension assembly 200 and an anvil assembly 50 (FIG. 34)

may be attached to the distal end 274b of the trocar 274 of the extension assembly 200 in a conventional manner. During actuation of the loading unit 40 and the anvil assembly 50, longitudinal advancement of the pusher member 190 of the second pusher assembly 180 of the adapter assembly 100, as described above, and as indicated by arrows "C" in FIG. 35A, causes longitudinal advancement of the outer flexible band assembly 230 of the extension assembly 200 and longitudinal advancement of the pusher member 170 of the first pusher assembly 160, as described above, and as indicated by arrows "D" in FIG. 35A, causes longitudinal advancement of the inner flexible band assembly 210. Rotation of the drive shaft 108 in a first direction, as described above, and as indicated by arrow "E", causes advancement of the trocar 274 of the extension assembly 200. Conversely, longitudinal retraction of the pusher member 190 causes longitudinal retraction of the outer flexible band assembly 230, longitudinal retraction of the pusher member 170 causes longitudinal retraction of the inner flexible band assembly 210, and rotation of the drive shaft 108 in a second direction causes retraction of the trocar 274 of the extension assembly 200.

In embodiments, the inner flexible band assembly 210 operably connects the second pusher assembly 180 of the adapter assembly 100 with a knife assembly (not shown) of the loading unit 40 (FIG. 34) of the end effector 30 (FIG. 34) attached to the connector assembly 290 of the extension assembly 200. The outer flexible band assembly 230 operably connects the first pusher assembly 160 of the adapter assembly 100 with a staple driver assembly (not shown) of the loading unit 40. The trocar assembly 270 operably connects the drive transfer assembly 130 of the adapter assembly 100 to the anvil assembly 50 (FIG. 34) of the end effector 30 (FIG. 34). In this manner, operation of the second pusher assembly 160 causes longitudinal movement of the inner flexible band assembly 210 which causes longitudinal movement of the knife assembly, operation of the first pusher assembly 180 causes longitudinal movement of the outer flexible band assembly 230 which causes longitudinal movement of the staple driver assembly, and operation of the drive transfer assembly 130 causes longitudinal movement of the trocar 274 which causes longitudinal movement of the anvil assembly 50 relative to the loading unit 40.

By stacking the first and second pusher assemblies 160, 180 of the adapter assembly 100, as described, and positioning the drive shaft 108 of the transfer assembly 130 through the first and second pusher assemblies 160, 180, the adapter assembly 100 can perform three functions through an access port or other opening (not shown) having a small diameter, e.g., 21 mm. Similarly, by configuring the inner flexible band assembly 210 within the outer flexible band assembly 230 and receiving the trocar assembly 270 through the inner and outer flexible band assemblies 210, 230, the extension assembly 200 can perform three functions through an access port or other opening (not shown) having a small diameter, e.g., 21 mm.

With reference now to FIGS. 36-45, an adapter assembly according to another embodiment of the present disclosure is shown as adapter assembly 300. Adapter assembly 300 is substantially similar to adapter assembly 100 described hereinabove and will only be described as relates to the differences therebetween.

As will become apparent from the following description, the configuration of adapter assembly 300 permits rotation of a distal portion 304 of adapter assembly 300 about a longitudinal axis "x" (FIG. 37), relative to a proximal portion 302 of adapter assembly 300. In this manner, an end effector, e.g. the end effector 30 (FIG. 34) secured to the distal portion 304 of the adapter assembly 300 or an end effector secured to an extension assembly, e.g., the extension assembly 200 (FIG. 17) which is secured to the distal portion 304 of the adapter assembly 300 is rotatable about the longitudinal axis "x" independent of movement of the surgical device (not shown) to which the adapter assembly 300 is attached.

Figure 36:
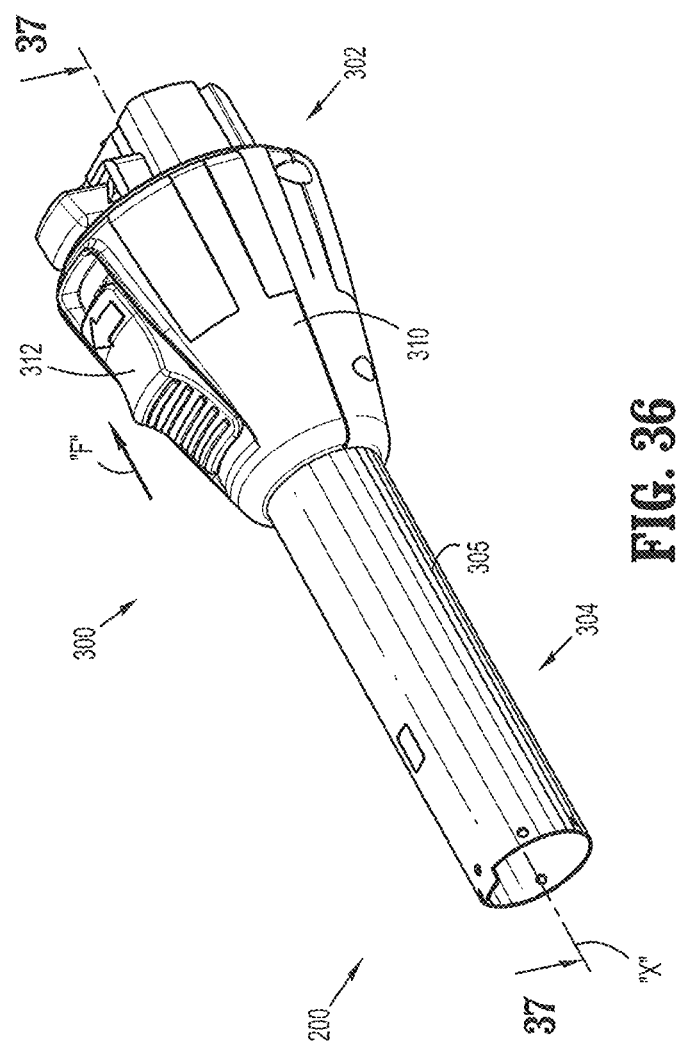
FIG. 36 is a perspective side view of an adapter assembly according to another embodiment of the present disclosure.
Figure 37:
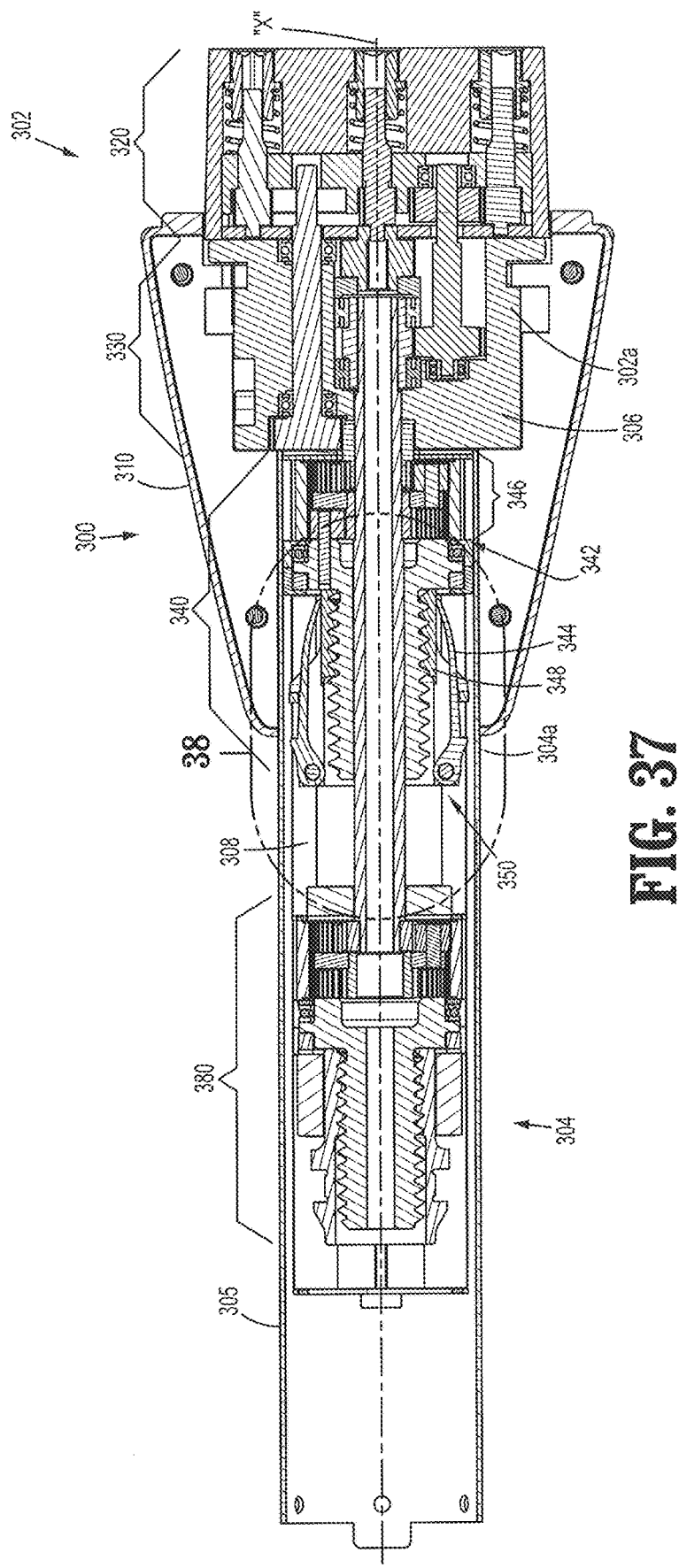
FIG. 37 is a cross-sectional side view taken along line 37-37 of FIG. 36.
Figure 38:
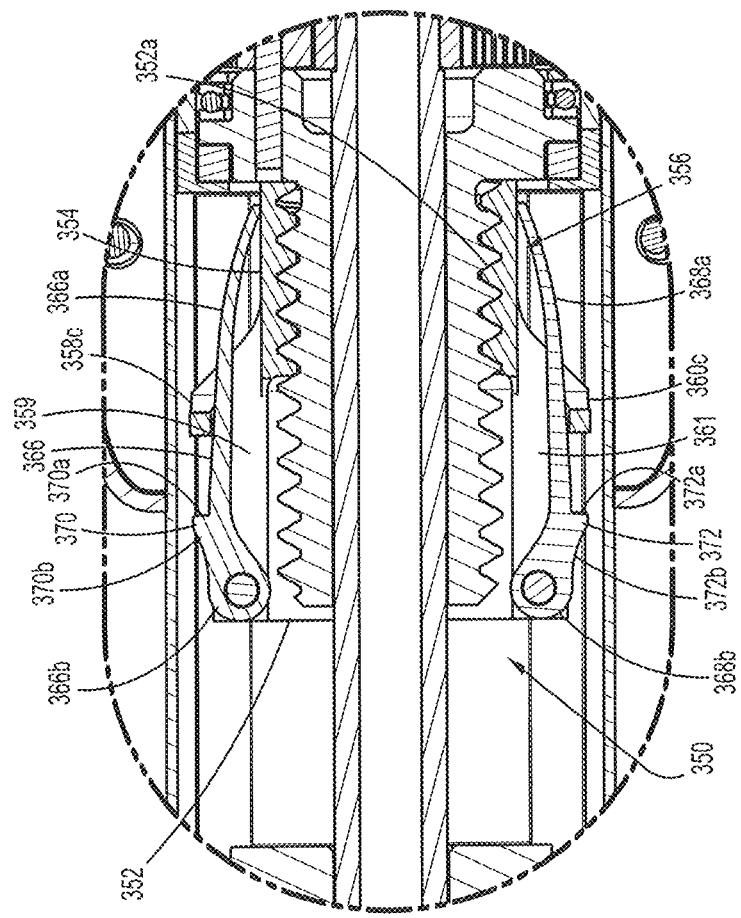
FIG. 38 is an enlarged cross-sectional side view of the indicated area of detail of FIG. 37.
Figure 39:
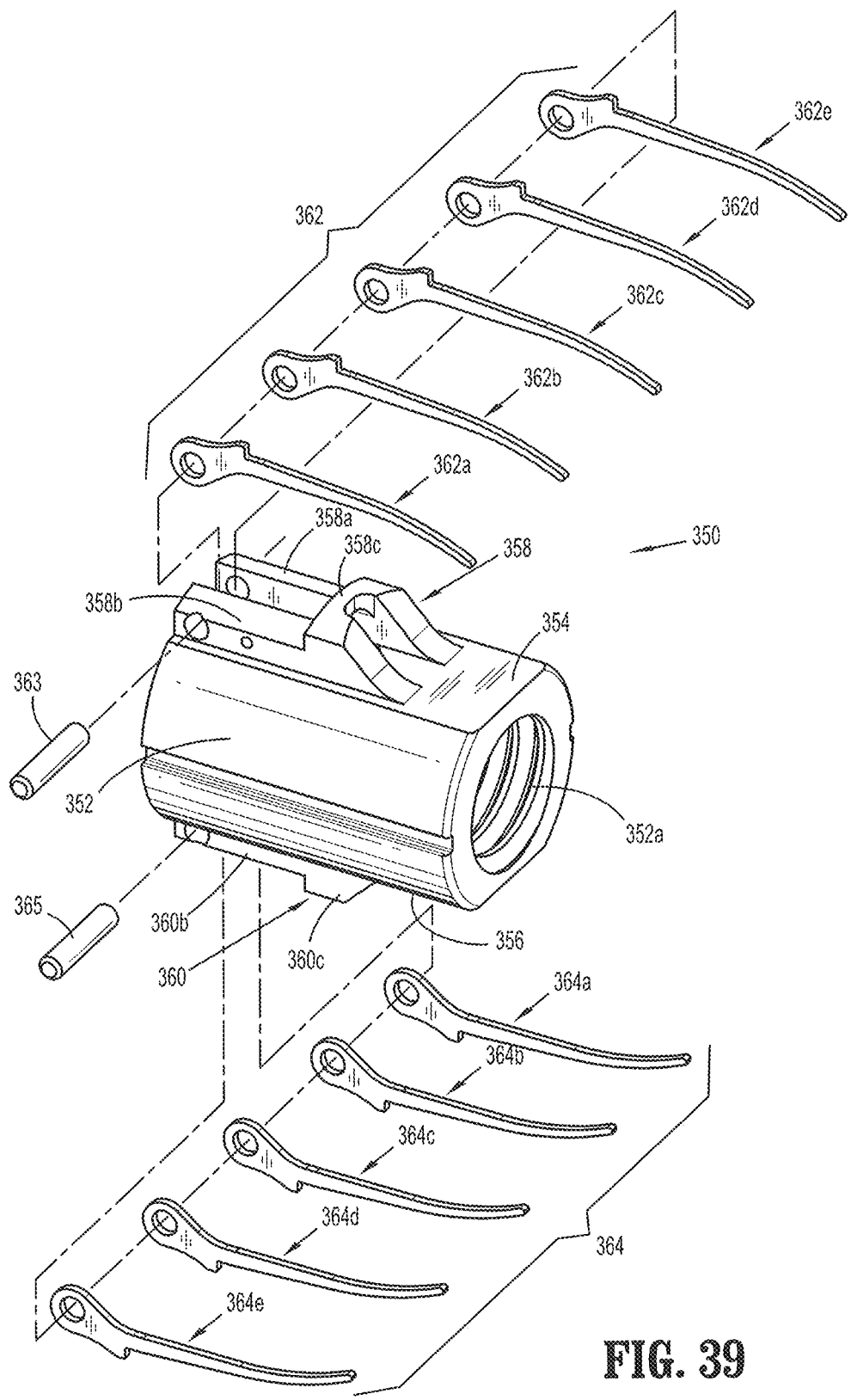
FIG. 39 is an exploded perspective view of a pusher assembly of the adapter assembly of FIG. 36.

With particular reference to FIG. 37, the adapter assembly 300 includes a base 306 and a support structure 308 rotatable relative to the base 306 along the longitudinal axis "x" of the adapter assembly 300. A rotation handle 310 is rotatably secured to the base 306 and is fixedly secured to a proximal end of support structure 308. The rotation handle 310 permits longitudinal rotation of the distal portion 304 of the adapter assembly 300 relative to the proximal end 302 of the adapter assembly 300. A latch 312 (FIG. 36) is mounted to the rotation handle 310 and selectively secures the rotation handle 310 in a fixed longitudinal position.

With reference still to FIG. 37, the proximal portion 302 of the adapter assembly 300 includes a drive coupling assembly 320 and a drive transfer assembly 330 operably connected to the drive coupling assembly 320. The distal portion 304 of the adapter assembly 300 includes a first pusher assembly 340 operably connected to the drive transfer assembly 330, and a second pusher assembly 380 operably connected to the drive transfer assembly 330. The drive coupling assembly 320 and the drive transfer assembly 330 are mounted within the base 306 and remain rotationally fixed relative to the surgical device (not shown) to which the adapter assembly 300 is attached. The first pusher assembly 340 and the second pusher assembly 380 are mounted within the support structure 308 and are rotatable relative to the surgical device (not shown) to which the adapter assembly 300 is attached.

The drive coupling assembly 320 is configured to selectively secure adapter assembly 300 to a surgical device (not shown). For a detailed description of an exemplary surgical device and drive coupling assembly, please refer to commonly owned U.S. patent application Ser. No. 14/550,183, filed Nov. 21, 2014, the content of which is incorporated by reference herein in its entirety.

With continued reference to FIGS. 36 and 37, the rotation handle 310 of the adapter assembly 300 is rotatably secured to the base 306. The latch 312 is configured to lock the rotation handle 310 relative to the base 306. Proximal movement of the latch 312, as indicated by arrow "F" in FIG. 36, disengages the latch 312 from the base 306 to permit rotation of the rotation handle 310 relative to the base 306. For a detailed description of an exemplary rotation handle and latch mechanism, please refer to commonly owned U.S. Provisional Patent Application Ser. No. 62/066,518 (now U.S. patent application Ser. No. 14/875,766, filed on Oct. 6, 2015), the content of which is incorporated by reference herein in its entirety.

The support structure 308 is fixedly received about the first and second drive pusher assemblies 340, 380 and is rotatable relative to the base 306. As noted above, the rotation handle 310 is fixedly secured to the proximal end of the support structure 308 to facilitate rotation of the support structure 308 relative to the base 306. The support structure 308 is retained within the outer sleeve 305 of the adapter assembly 300 and is configured to maintain axial alignment of the first and second drive pusher assemblies 340, 380. For a detailed description of an exemplary support structure, please refer to commonly owned U.S. Provisional Patent Application Ser. No. 62/066,518, the content of which was previously incorporated by reference herein.

The drive transfer assembly 330, the first pusher assembly 340, and the second drive pusher assembly 380 of the adapter assembly 300 are substantially identical to the respective drive transfer assembly 130, first pusher assembly 160, and second drive pusher assembly 180 of the adapter assembly 100 described hereinabove, and therefore, will only be described as relates to the differences therebetween.

Briefly, the first pusher assembly 340 includes a planetary gear assembly 346 operably supported within a proximal housing section 342 and a screw member 348 operably connected to the planetary gear assembly 346 and rotatably supported within a distal housing section 344. The first pusher assembly 340 further includes a pusher member 350 operably connected to the screw member 348 and slidably disposed within the distal housing section 344.

With particular reference to FIGS. 38-41, the pusher member 350 includes a substantially cylindrical body 352 having a threaded proximal inner surface 352a and opposed planar outer surfaces 354, 356. Retainers 358, 360 extend from the respective planar outer surfaces 354, 356. Each of the retainers 358, 360 includes a pair of elongate flanges 358a, 358b, 360a, 360b, respectively, and a connector 358c, 360c, respectively, connecting a proximal end of the elongate flanges 358a, 358b, 360a, 360b, respectively. Each of the retainers 358, 360 defines a longitudinal slot 359, 361, respectively, between respective elongate flanges 358a, 358b, 360a, 360b.

A pawl assembly 362, 364 is received within each of the longitudinal slots 359, 361, respectively. The pawl assemblies 362, 364 each include a plurality of pawl members 362a-e, 364a-e, respectively (collectively, pawls 366, 368, respectively), and pivot pins 363, 365. The pawls 366, 368 are secured within the respective longitudinal slots 359, 361 by the pivot pins 363, 365, respectively, received through openings 367, 369, respectively, formed in the respective distal ends 366b, 368b of the pawls 366, 368, respectively. The pawls 366, 368 each include a curved profile and are formed of a resilient material. Protrusions 370, 372 are formed on an outer curved surface of the respective pawls 366, 368 proximal to the distal ends 366b, 368b, respectively. The protrusions 370, 372 each include a flat proximal facing surface 370a, 372a, respectively, and a slanted or inclined distal facing surface 370b, 372b. As will be described in further detail below, the protrusions 370, 372 are configured to be received within openings 241, 243 (FIG. 43) of respective connector extensions 240, 242 (FIG. 43) of outer flexible band 230 (FIG. 42) of the extension assembly 200 (FIG. 42) to secure the outer flexible band 230 to the pusher member 350 of the first pusher assembly 340 when the extension assembly 200 is secured to the adapter assembly 300.

Figure 40:
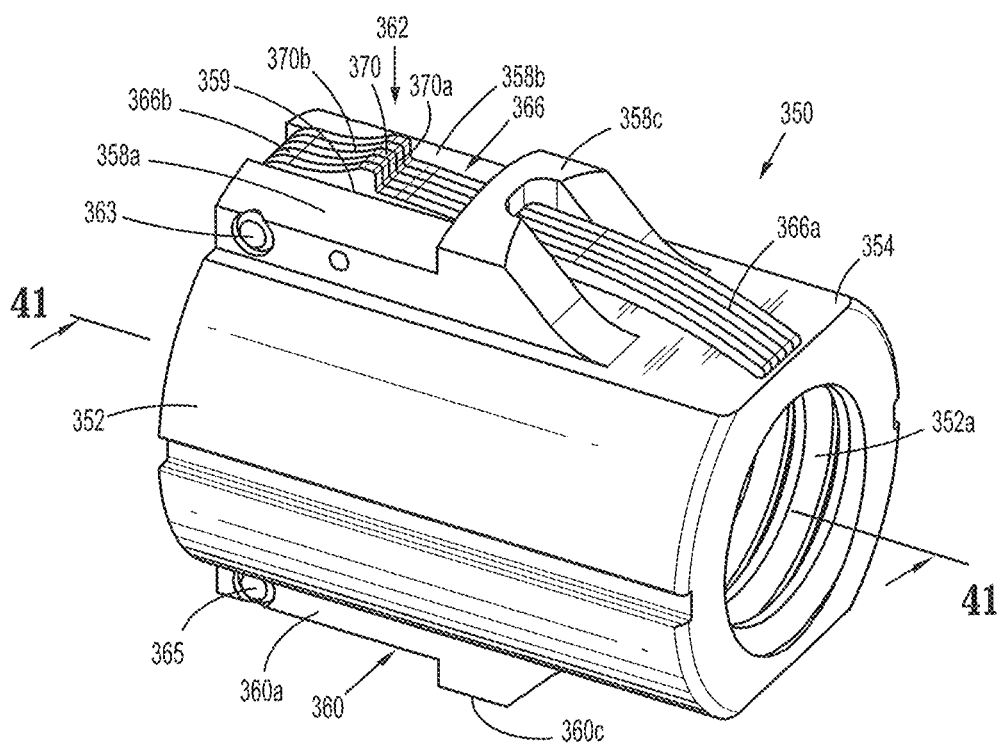
FIG. 40 is a perspective side view of the pusher assembly of FIG. 39.
Figure 41:
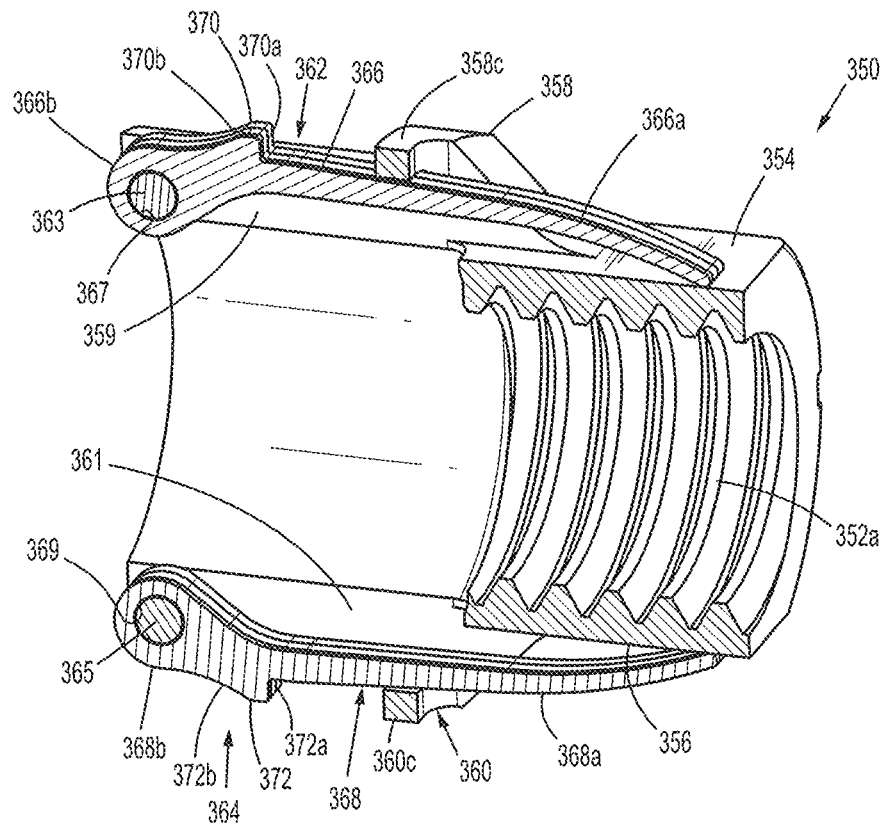
FIG. 41 is a cross-sectional side view taken along line 41-41 of FIG. 40.
Figure 44:
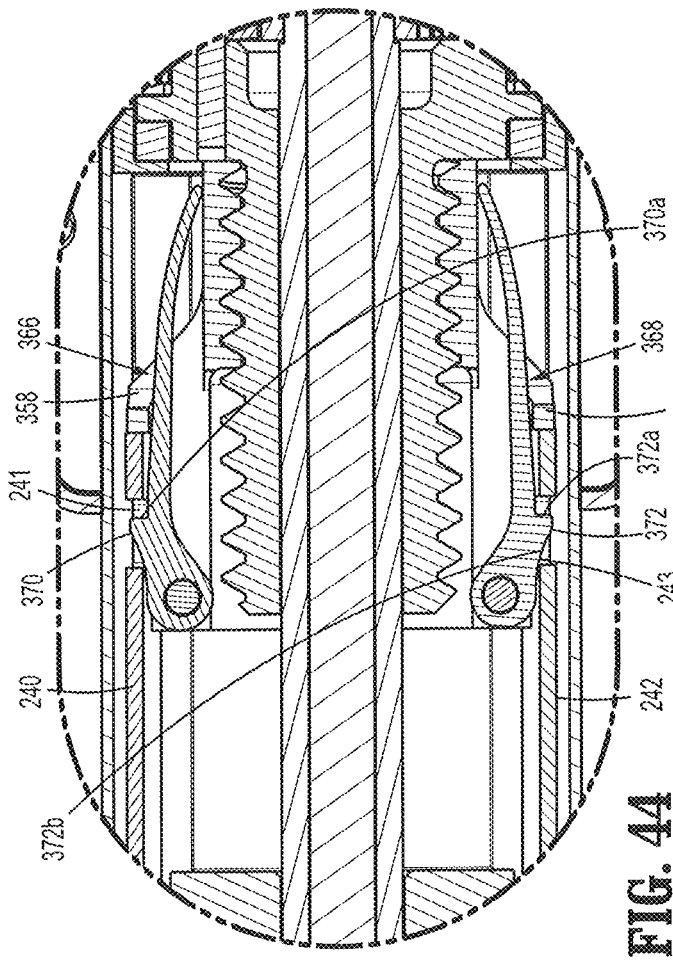
FIG. 44 is an enlarged cross-sectional top view of the indicated area of detail of FIG. 42, with the extension assembly secured to the adapter assembly.
Figure 45:
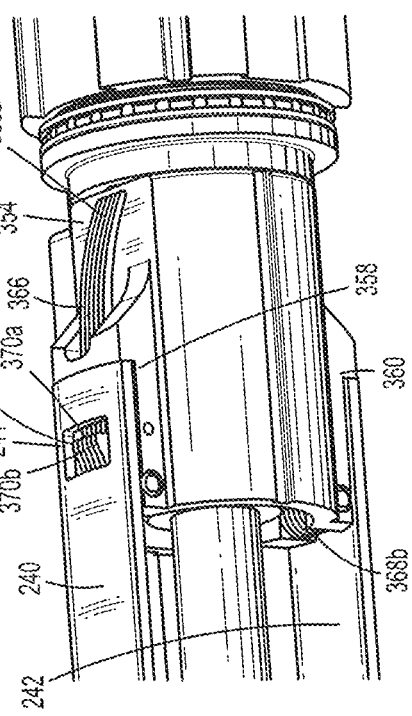
FIG. 45 is a perspective side view of the adapter assembly and extension assembly of FIG. 42, with outer sleeves removed.

With particular reference to FIGS. 40 and 41, the pawls 366, 368 of the pawl assemblies 362, 364, respectively, are received within respective longitudinal slots 359, 361 of retainers 358, 360, respectively, with the respective distal ends 366b, 368b secured to retainers 358, 360, respectively, by pivot pins 363, 365, respectively. The proximal ends 366a, 368a of the pawls 366, 368, respectively, are received under the respective connectors 358c, 360c of the retainers 358, 360, respectively, and engage the planar surfaces 354, 356, respectively, of the cylindrical body 352 of the pusher member 350. The pawls 366, 368 are configured such that the protrusions 370, 372, respectively, extend above the elongate flanges 358a, 358b, 360a, 360b, respectively, of the retainers 358, 360, respectively, when the respective pawls 366, 368 are in a first or initial position (FIG. 40).

With reference now to FIGS. 42 and 43, the curved profile of pawls 366, 368 is such that an inward force applied to the protrusions 370, 372, respectively, when the respective inclined distal surfaces 370b, 372b are engaged by connector extensions 240, 242, respectively, of outer flexible band 230 (FIG. 42) of the extension assembly 200 (FIG. 42) cause the pawls 366, 368 to flex inwardly. As the pawls 366, 368 flex inwardly the protrusions 370, 372, respectively, are positioned below the respective retainers 358, 360, thereby allowing connector extensions 240, 242 of outer flexible band 230 to pass over the respective retainers 358, 360. Once the openings 241, 243 of respective connector extensions 240, 242 align with the protrusions 370, 372, respectively, of the respective pawls 366, 368, the pawls 366, 368, respectively spring back to the initial position (FIG. 45), causing the protrusions 370, 372, respectively, to be received within the respective openings 241, 243 of the connector extensions 240, 242, respectively, such that the outer flexible band 230 (FIG. 42) of the extension assembly 200 (FIG. 42) is secured to the first pusher member 340.

Once the connector extensions 240, 242 of the outer flexible band 230 of the extension assembly 200 are received over the pawls 366, 368, respectively, and once the protrusions 370, 372 are received within respective openings 241, 243 of the respective connector extensions 240, 242, engagement of the connector extensions 240, 242 by the flat proximal surface 370a, 372a of the protrusions 370, 372, respectively, prevents the connector extensions 240, 242 from being disengaging from the first pusher assembly 340 during operation of the adapter assembly 300 and the extension assembly 200.

The adapter assembly 300 operates in a substantially similar manner to adapter assembly 100 described hereinabove. In addition, adapter assembly 300 is configured to permit rotation of an end effector, e.g., end effector 30 (FIG. 34) attached to adapter assembly 300 or attached to an extension assembly that is attached to adapter assembly 300 to be selectively rotated about longitudinal axis "x" (FIG. 36) during use.

Any of the components described herein may be fabricated from either metals, plastics, resins, composites or the like taking into consideration strength, durability, wearability, weight, resistance to corrosion, ease of manufacturing, cost of manufacturing, and the like.

With reference now to FIGS. 46-48, a pusher member, in accordance with another embodiment of the present disclosure, is generally designated as 400. Pusher member 400 may be utilized in adapter assemblies 100 and/or 300 in place of any of pusher members 170, 190, and/or 350.

Pusher member 400 includes a composite body 410 that is formed of two or more materials to reduce the input torque required to longitudinally advance and retract the pusher member 400 while providing sufficient strength to distribute the load against the inner and/or outer flexible band assemblies 210, 230 (see e.g., FIGS. 18-19) of the extension assembly (see e.g., FIG. 17) to effect a function of an end effector (see e.g., FIG. 34), as described above. The composite body 410 includes an outer housing 420, a threaded insert 440 disposed within and keyed to the outer housing 420, and a retaining ring 450 secured to the outer housing 420 for retaining the threaded insert 440 within the outer housing 420.

The outer housing 420 includes a proximal housing region 422 having a central bore 422a defined in an inner surface 424 of the proximal housing region 422, and longitudinal apertures 422b defined through the inner surface 424 and an outer surface 426 of the proximal housing region 422 in opposed relation relative to each other. Proximal tabs 428 are formed on a distal end of the proximal housing region 422 in opposed relation relative to each other. The proximal tabs 428 protrude laterally from the outer surface 426 of the outer housing 420 to push and/or aid in the longitudinal advancement of the connector extensions 240, 242 of the outer flexible band assembly 230 (see e.g., FIG. 19) or the connector extensions 220, 224 of the inner flexible band assembly 220 (see e.g., FIG. 18) of the extension assembly 200 (see e.g., FIG. 17) depending upon the pusher assembly 160, 180, 340, and/or 380 (see e.g., FIGS. 12, 15, 37) with which the pusher member 400 is used.

The outer housing 420 includes a distal housing region 430 having a central bore 430a defined in an inner surface 432 of the distal housing region 430. The central bore 430a of the distal housing region 430 is smaller in dimension than the central bore 422a of the proximal housing region 422 such that an end wall 434 of the distal housing region 430 is disposed at a distal end of the central bore 422a of the proximal housing region 422. Distal tabs 436 are formed on the distal housing region 430 in opposed relation relative to each other. The distal tabs 436 are longitudinally aligned with the proximal tabs 428, and are disposed in spaced relation relative to the proximal tabs 428. The distal tabs 436 protrude laterally from the outer housing 420 to engage and move the connector extensions 240, 242 of the outer flexible band assembly 230 (see e.g., FIG. 19) or the connector extensions 220, 224 of the inner flexible band assembly 220 (see e.g., FIG. 18) of the extension assembly 200 (see e.g., FIG. 17), as described above.

The threaded insert 440 includes a body portion 442 configured and dimensioned to be retained with the central bore 422a of the proximal housing region 422 of the outer housing 420. The body portion 442 of the threaded insert 440 has a threaded central bore 442a defined through an inner surface 444 of the body portion 442 that is configured to threadingly engage the screw member 168, 188, or 348 of the pusher assembly 160, 180, or 340 (see e.g., FIGS. 12, 15, 37) with which the pusher member 400 is used, to axially move the pusher member 400, as described above. The body portion 442 of the threaded insert 440 includes longitudinal rails 446 formed on an outer surface 448 of the body portion 442 in opposed relation relative to each other, and protrude laterally therefrom. The longitudinal rails 446 are configured and dimensioned to engage and extend laterally through the longitudinal apertures 422b of the proximal housing region 422 of the outer housing 420 to prevent rotational movement of the threaded insert 440 relative to the outer housing 420. The longitudinal rails 446 extend laterally beyond the outer wall 426 of the proximal housing region 422 of the outer housing 420 and are keyed to the distal housing section 164, 184, or 344 of the pusher assembly 160, 180, or 340 (see e.g., FIGS. 12, 15, 37) in which the pusher member 400 is used, such that the pusher member 400 is slidably disposed within the distal housing section 164, 184, or 344.

The retaining ring 450 includes an annular body 452 defining an opening 452a therethrough. The opening 452a of the retaining ring 450 has a cross-sectional dimension that is substantially the same as the cross-sectional dimension of the central bore 422a of the proximal housing region 422 of the outer housing 420 to allow uninhibited engagement of the screw member 168, 188, or 348 of the pusher assembly 160, 180, or 340 (see e.g., FIGS. 12, 15, 37) with which the pusher member 400 is used, with the threaded central bore 442a of the threaded insertion 440 of the pusher member 400. The retaining ring 450 is fixedly secured to the outer housing 420, to lock the threaded insert 440 between the end wall 434 of the distal housing region 430 of the outer housing 420 and the retaining ring 450, to prevent axial movement of the threaded insert 440 relative to the outer housing 420. The retaining ring 450 may be secured to the outer housing 420 by welding, swaging, staking, crimping, soldering, brazing, bonding (e.g., gluing or cementing), and/or mechanical fastening (e.g., riveting, pinning, bayonet coupling, barb fitting, etc.), among other securing techniques within the purview of those skilled in the art.

The outer housing 420 is integrally and/or monolithically formed of a first material. The first material is a metal such as, for example, stainless steel, to provide load supporting strength for effecting a function of an end effector of the presently described surgical devices. The threaded insert 440 is integrally and/or monothically formed of a second material. The second material is a polymer such as, for example, polyether ether ketone (PEEK), to reduce the input torque for advancing the pusher member 400. The retaining ring 450 is integrally and/or monolithically formed of a third material. The third material is a metal which may be the same as, or different from, the first material of the outer housing 420.

The threaded insert 440 is formed of any suitable polymeric material to reduce friction forces generated between the inner surface 444 of the threaded insert 440 and the screw member 168, 188, or 348 of the pusher assembly 160, 180, or 340 (see e.g., FIGS. 12, 15, 37) with which the pusher member 400 is used, as well as between the longitudinal rails 446 of the threaded insert 440 and the distal housing section 164, 184, or 344 (see e.g., FIGS. 12, 15, 37), thereby improving the efficiency of the pusher member 400 over pusher members formed entirely of metal. The outer housing 420 is formed of any suitable metallic material to distribute the load across a larger area, thereby reducing the stress on the threaded insert 440 and allowing the pusher member 400 to push at a greater force than a pusher member made entirely of a polymer.

While each of the outer housing 420, the threaded insert 440, and the retaining ring 450 of the pusher member 400 is described as being integrally and/or monolithically formed, it should be understood that one or more portions of the outer housing 420, the threaded insert 440, and/or the retaining ring 450 can be separately formed of any suitable metallic and/or polymeric material and affixed to the respective component. Persons skilled in the art will understand that one or more of any of the components, or portions thereof, can be formed using known forming and/or fastening techniques such as molding, casting, milling, welding, etc. For example, the outer housing 420 and the retaining ring 450 can be casted and/or milled, the threaded insert 440 can be injection molded in the outer housing 420, and the retaining ring 450 can be welded to the outer housing 420.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical assembly for operably connecting an end effector to an electrosurgical instrument, the surgical assembly comprising:
   an adapter assembly including:
      a drive coupling assembly;
      a drive transfer assembly operably received through the drive coupling assembly and including first and second rotatable shafts;
      a first pusher assembly operably connected to the first rotatable shaft for converting rotational motion from the first rotatable shaft to longitudinal movement to perform a first function, the first pusher assembly including a first pusher member having an outer housing formed of a first material, and a threaded insert formed of a second material and disposed within and coaxial with the outer housing, wherein the threaded insert is axially and rotationally fixed relative to the outer housing; and
      a second pusher assembly operably connected to the second rotatable shaft for converting rotational motion from the second rotatable shaft to longitudinal movement to perform a second function, the second pusher assembly including a second pusher member having an outer housing formed of a first material, and a threaded insert formed of a second material; and
   an extension assembly operably connected to a distal end of the adapter assembly, the extension assembly including a flexible band assembly releasably secured to the first pusher member of the first pusher assembly.

2. The surgical assembly of claim 1, wherein the first material of the outer housing is a metal.

3. The surgical assembly of claim 2, wherein the second material of the threaded insert is a polymer.

4. The surgical assembly of claim 3, wherein the metal is stainless steel.

5. The surgical assembly of claim 4, where the polymer is polyether ether ketone.

6. The surgical assembly of claim 1, wherein the outer housing of the first pusher member includes first and second distal tabs extending laterally therefrom.

7. The surgical assembly of claim 6, wherein the flexible band assembly includes first and second connector members, and each of the first and second connector members is configured to engage a respective one of the first and second distal tabs.

8. The surgical assembly of claim 1, wherein the threaded insert of the first pusher member includes an inner surface defining a threaded central bore.

9. The surgical assembly of claim 8, wherein the adapter assembly includes a screw member threadingly engaged with the inner surface of the threaded insert of the first pusher member.

10. The surgical assembly of claim 1, wherein the outer housing includes first and second apertures disposed therethrough, and the threaded insert includes an outer surface having first and second longitudinal rails extending laterally therefrom, and each of the first and second longitudinal rails of the threaded insert are keyed to a respective one of the first and second apertures of the outer housing.

11. The surgical assembly of claim 1, further including a drive member operably connected to a third rotatable shaft of the drive transfer assembly for transferring rotational motion from the third rotatable shaft to perform a third function.

12. The surgical assembly of claim 1, wherein the first material is different from the second material.

13. A surgical assembly for operably connecting an end effector to an electrosurgical instrument, the surgical assembly comprising:
   an adapter assembly including,
      a drive coupling assembly;
      a drive transfer assembly operably received through the drive coupling assembly and including a first rotatable shaft; and
      a first pusher assembly operably connected to the first rotatable shaft for converting rotational motion from the first rotatable shaft to longitudinal movement to perform a first function, the first pusher assembly including a first pusher member having an outer housing formed of a first material, and a threaded insert formed of a second material and disposed within the outer housing, wherein the outer housing of the first pusher member includes:
         first and second distal tabs extending laterally therefrom; and
         first and second proximal tabs extending laterally therefrom, wherein each of the first and second proximal tabs is aligned with a respective one of the first and second distal tabs; and
   an extension assembly operably connected to a distal end of the adapter assembly, the extension assembly including a flexible band assembly operably connectable to the first pusher member of the first pusher assembly, wherein the flexible band assembly includes first and second connector members, and each of the first and second connector members is configured to engage a respective one of the first and second distal tabs.

14. A surgical assembly for operably connecting an end effector to an electrosurgical instrument, the surgical assembly comprising:
   an adapter assembly including,
      a drive coupling assembly;
      a drive transfer assembly operably received through the drive coupling assembly and including a first rotatable shaft; and
      a first pusher assembly operably connected to the first rotatable shaft for converting rotational motion from the first rotatable shaft to longitudinal movement to perform a first function, the first pusher assembly including a first pusher member having an outer housing formed of a first material, a threaded insert formed of a second material and disposed within the outer housing, and a retaining ring fixedly secured to a proximal end of the outer housing to secure the threaded insert within the outer housing; and
   an extension assembly operably connected to a distal end of the adapter assembly, the extension assembly including a flexible band assembly operably connectable to the first pusher member of the first pusher assembly.

15. The surgical assembly of claim 14, wherein the retaining ring is formed of a third material.

16. The surgical assembly of claim 15, wherein the third material of the retaining ring is a metal.

17. The surgical assembly of claim 16, wherein the metal is stainless steel.

18. A surgical assembly for operably connecting an end effector to an electrosurgical instrument, the surgical assembly comprising:
   an adapter assembly including:
      a drive coupling assembly;
      a drive transfer assembly operably received through the drive coupling assembly and including first and second rotatable shafts;

a first pusher assembly operably connected to the first rotatable shaft for converting rotational motion from the first rotatable shaft to longitudinal movement to perform a first function, the first pusher assembly including a first pusher member having an outer housing formed of a first material, and a threaded insert formed of a second material and disposed within the outer housing, wherein the threaded insert is axially and rotationally fixed relative to the outer housing; and a second pusher assembly operably connected to the second rotatable shaft for converting rotational motion from the second rotatable shaft to longitudinal movement to perform a second function, the second pusher assembly being disposed distal of the first pusher assembly; and an extension assembly operably connected to a distal end of the adapter assembly, the extension assembly including a flexible band assembly releasably secured to the first pusher member of the first pusher assembly.

19. The surgical assembly of claim 18, wherein the second pusher assembly includes a second pusher member having an outer housing formed of a first material, and a threaded insert formed of a second material.

20. The surgical assembly of claim 19, wherein the first material is different from the second material.

* * * * *